United States Patent
Childress et al.

(10) Patent No.: US 12,053,554 B2
(45) Date of Patent: Aug. 6, 2024

(54) ULTRAVIOLET LIGHT-EMITTING MODULE AND DISINFECTING SYSTEM

(71) Applicant: The Boeing Company, Chicago, IL (US)

(72) Inventors: Jamie J. Childress, Mercer Island, WA (US); Arthur E. Brockschmidt, Jr., Renton, WA (US)

(73) Assignee: The Boeing Company, Arlington, VA (US)

( * ) Notice: Subject to any disclaimer, the term of this patent is extended or adjusted under 35 U.S.C. 154(b) by 345 days.

(21) Appl. No.: 17/452,561

(22) Filed: Oct. 27, 2021

(65) Prior Publication Data
US 2022/0184250 A1 Jun. 16, 2022

Related U.S. Application Data

(60) Provisional application No. 63/154,239, filed on Feb. 26, 2021, provisional application No. 63/124,341, filed on Dec. 11, 2020.

(51) Int. Cl.
*A61L 2/10* (2006.01)

(52) U.S. Cl.
CPC .............. *A61L 2/10* (2013.01); *A61L 2202/11* (2013.01); *A61L 2202/122* (2013.01)

(58) Field of Classification Search
CPC .. A61L 2/10; A61L 2202/11; A61L 2202/122; A61L 9/20; A61L 2202/16;
(Continued)

(56) References Cited

U.S. PATENT DOCUMENTS

| | | | |
|---|---|---|---|
| 5,498,394 A | | 3/1996 | Matschke |
| 6,144,175 A | * | 11/2000 | Parra .................. H05B 41/3921 |
| | | | 315/307 |

(Continued)

FOREIGN PATENT DOCUMENTS

| | | |
|---|---|---|
| CA | 2967190 A1 | 5/2016 |
| CA | 3123597 A1 | 6/2020 |

(Continued)

OTHER PUBLICATIONS

European Patent Office, Office Action Issued in Application No. 21210726.2, Sep. 14, 2023, Germany, 9 pages.
(Continued)

*Primary Examiner* — David E Smith
*Assistant Examiner* — Christopher J Gassen
(74) *Attorney, Agent, or Firm* — Alleman Hall & Tuttle LLP

(57) ABSTRACT

Modules, systems and methods that disinfect surfaces using ultraviolet (UV) light are disclosed. In one aspect, a UV light-emitting module comprises an enclosure including an aluminum rear wall comprising a ventilation opening and a face plate spaced from the rear wall and comprising a light-transmitting aperture. Four aluminum sidewalls extend between the rear wall and the face plate, with at least one sidewall comprising a ventilation opening. At least one fluoropolymer UV light emitter support within the enclosure seats a plurality of UV light emitters that each comprise an elongated lamp comprising a first end having a first terminal and an opposing second end having a second terminal. Lead wires electrically couple the terminals of the elongated lamps to a power source.

20 Claims, 20 Drawing Sheets

(58) Field of Classification Search
CPC .... A61L 2202/25; A61L 2209/15; A61L 2/26; F24F 8/22; B64D 11/02; B64D 11/04; B64F 5/30; H01J 65/046
See application file for complete search history.

(56) References Cited

U.S. PATENT DOCUMENTS

| | | | |
|---|---|---|---|
| 6,656,424 | B1 | 12/2003 | Deal |
| 7,595,723 | B2 | 9/2009 | Heitzmann et al. |
| 8,581,522 | B2 | 11/2013 | Inskeep |
| 8,791,441 | B1 | 7/2014 | Lichtblau |
| 9,623,133 | B2 | 4/2017 | Childress et al. |
| 11,382,993 | B2 | 7/2022 | Childress |
| 2004/0249369 | A1 | 12/2004 | Muzzi et al. |
| 2008/0152548 | A1* | 6/2008 | Clark ................. A61L 9/205 422/121 |
| 2008/0289800 | A1 | 11/2008 | Simadiris et al. |
| 2009/0045750 | A1 | 2/2009 | Brggs et al. |
| 2011/0243789 | A1 | 10/2011 | Roberts |
| 2012/0076702 | A1 | 3/2012 | Dunkley et al. |
| 2012/0168641 | A1* | 7/2012 | Lizotte ................. C02F 1/325 250/503.1 |
| 2012/0240968 | A1 | 9/2012 | Schumacher |
| 2012/0305787 | A1 | 12/2012 | Henson |
| 2013/0330235 | A1 | 12/2013 | Stibich et al. |
| 2014/0044590 | A1 | 2/2014 | Trapani |
| 2014/0175280 | A1 | 6/2014 | Tantillo |
| 2015/0064065 | A1 | 3/2015 | Kreitenberg |
| 2015/0165079 | A1* | 6/2015 | Shur ................. A61L 2/10 250/455.11 |
| 2015/0235727 | A1 | 8/2015 | Lott et al. |
| 2016/0271288 | A1 | 9/2016 | Davis |
| 2016/0324996 | A1* | 11/2016 | Bilenko ................. A61L 2/24 |
| 2017/0198896 | A1* | 7/2017 | May ................. F21V 29/89 |
| 2018/0064833 | A1 | 3/2018 | Childress et al. |
| 2018/0133351 | A1 | 5/2018 | Smetona et al. |
| 2018/0243582 | A1 | 8/2018 | Kaneda et al. |
| 2018/0339075 | A1 | 11/2018 | Kennedy et al. |
| 2019/0142981 | A1 | 5/2019 | Kim et al. |
| 2019/0300174 | A1 | 10/2019 | Young et al. |
| 2020/0061223 | A1 | 2/2020 | Hallack |
| 2020/0234941 | A1 | 6/2020 | Yagyu et al. |
| 2021/0213147 | A1* | 7/2021 | Donhowe ............. C02F 1/325 |
| 2021/0346540 | A1 | 11/2021 | Childress et al. |
| 2021/0346541 | A1 | 11/2021 | Callahan et al. |
| 2021/0346561 | A1 | 11/2021 | Callahan et al. |
| 2021/0361794 | A1* | 11/2021 | Yencho ................. A61L 2/26 |
| 2021/0386882 | A1 | 12/2021 | Brockschmidt, Jr. et al. |
| 2021/0386883 | A1 | 12/2021 | Childress |
| 2021/0386884 | A1 | 12/2021 | Brockschmidt, Jr. et al. |
| 2021/0396918 | A1 | 12/2021 | Gross et al. |
| 2022/0023458 | A1 | 1/2022 | Brockschmidt, Jr. et al. |
| 2022/0023459 | A1 | 1/2022 | Colletti et al. |
| 2022/0023478 | A1 | 1/2022 | Childress |
| 2022/0068627 | A1* | 3/2022 | Yagyu ................. H01J 61/547 |
| 2022/0111086 | A1 | 4/2022 | Childress |
| 2022/0111087 | A1 | 4/2022 | Childress et al. |
| 2022/0111096 | A1 | 4/2022 | Childress |
| 2022/0113006 | A1 | 4/2022 | Childress et al. |
| 2022/0133925 | A1 | 5/2022 | Gray et al. |
| 2022/0184252 | A1 | 6/2022 | Childress et al. |

FOREIGN PATENT DOCUMENTS

| | | |
|---|---|---|
| CN | 106049005 A | 10/2016 |
| CN | 211204004 U | 8/2020 |
| CN | 111744026 A | 10/2020 |
| JP | H09201401 A | 8/1997 |
| JP | 2000283840 A | 10/2000 |
| JP | 2018055965 A | 4/2018 |
| JP | 2018092755 A | 6/2018 |
| JP | 2018167166 A | 11/2018 |
| KR | 20150045628 A | 4/2015 |
| WO | 2012142427 A1 | 10/2012 |
| WO | 2015028334 A1 | 3/2015 |
| WO | 2016210399 A2 | 12/2016 |
| WO | 2020052506 A1 | 3/2020 |

OTHER PUBLICATIONS

European Patent Office, Office Action Issued in Application No. 21210723.9, Sep. 19, 2023, Germany, 5 pages.
European Patent Office, Office Action Issued in Application No. 21210728.8, Sep. 20, 2023, Germany, 5 pages.
European Patent Office, Extended European Search Report Issued in Application No. 21210725.4, Sep. 6, 2022, Germany, 79 pages.
European Patent Office, Extended Search Report Issued in Application No. 21210726.2, Sep. 8, 2022, Germany, 52 pages.
European Patent Office, Extended Search Report Issued in Application No. 21210727.0, Sep. 9, 2022, Germany, 16 pages.
European Patent Office, Extended Search Report Issued in Application No. 21210723.9, Sep. 23, 2022, Germany, 21 pages.
European Patent Office, Extended European Search Report Issued in Application No. 21210728.8, Sep. 28, 2022, Germany, 13 pages.
Welch, D. et al., "Far-UVC light: A new tool to control the spread of airborne-mediated microbial diseases," Scientific Reports, vol. 8, No. 1, Feb. 9, 2018, 7 pages.
Ushio Care222, Far UV-C Disinfection Technology, Ushio, Oct. 3, 2020, 5 pages.
European Patent Office, Partial European Search Report Issued in Application No. 21210723.9, May 12, 2022, Germany, 16 pages.
European Patent Office, Partial European Search Report Issued in Application No. 21210728.8, Jun. 9, 2022, Germany, 14 pages.
Plass, C. et al., "Ultraviolet Wand," U.S. Appl. No. 29/735,235, filed May 19, 2020, 800-434DES, 15 pages.
Barrett, L et al., "Sterilization of sea lice eggs with ultraviolet C light: towards a new preventative technique for aquaculture," Post Management Science, vol. 76, No. 3, Mar. 2020, 7 pages.
European Patent Office, Extended European Search Report issued in application No. 21202296.6, May 24, 2022, Germany, 11 pages.
European Patent Office, Extended European Search Report issued in application No. 21207466.0, May 2, 2022, Germany, 8 pages.
European Patent Office, Extended European Search Report issued in application No. 21210410.03, Apr. 25, 2022, Germany, 10 pages.
Honeywell UV Treatment System, Available online at https://aerospace.honeywell.com/en/learn/products/cabin/uv-cabin-system, Available as early as Jun. 21, 2021, 4 pages.
Huang, B. et al., "Research on UV radiation measurements and correction methods," Proceedings of the International Symposium on Photoelectronic Detection and Imaging, May 24, 2011, Beijing, China, 10 pages.
USA United States Patent Office, Written Opinion issued in application No. PCT/US2016/039506, May 31, 2017, WIPO, 8 pages.
European Patent Office, partial European Search Report issued in application No. 21202296.6, Mar. 4, 2022, Germany, 11 pages.
UVC Sensors to Monitor Ultraviolet Germicidal Irradiation (UVGI), Available online at https://www.pro-lite.co.uk/File/Solar%20Light%20UVGI%20Radiometer%20Brochure.pdf, Jan. 2019, 2 pages.
European Patent Office, Partial European Search Report Issued in Application No. 21210725.4, Apr. 26, 2022, Germany, 16 pages.
European Patent Office, Partial European Search Report Issued in Application No. 21210726.2, May 3, 2022, Germany, 17 pages.
European Patent Office, Partial European Search Report Issued in Application No. 21210727.0, May 4, 2022, Germany, 16 pages.
Buonanno, M. et al., "Far-UVC light (222nm) efficiently and safely inactivates airborne human coronaviruses," Scientific Reports, vol. 10, Jun. 24, 2020, 8 pages.
United States Patent and Trademark Office, Office Action Issued in U.S. Appl. No. 17/452,559, Feb. 1, 2024, 39 pages.
United States Patent and Trademark Office, Notice of Allowance Issued in U.S. Appl. No. 17/452,560, Mar. 1, 2024, 41 pages.

* cited by examiner

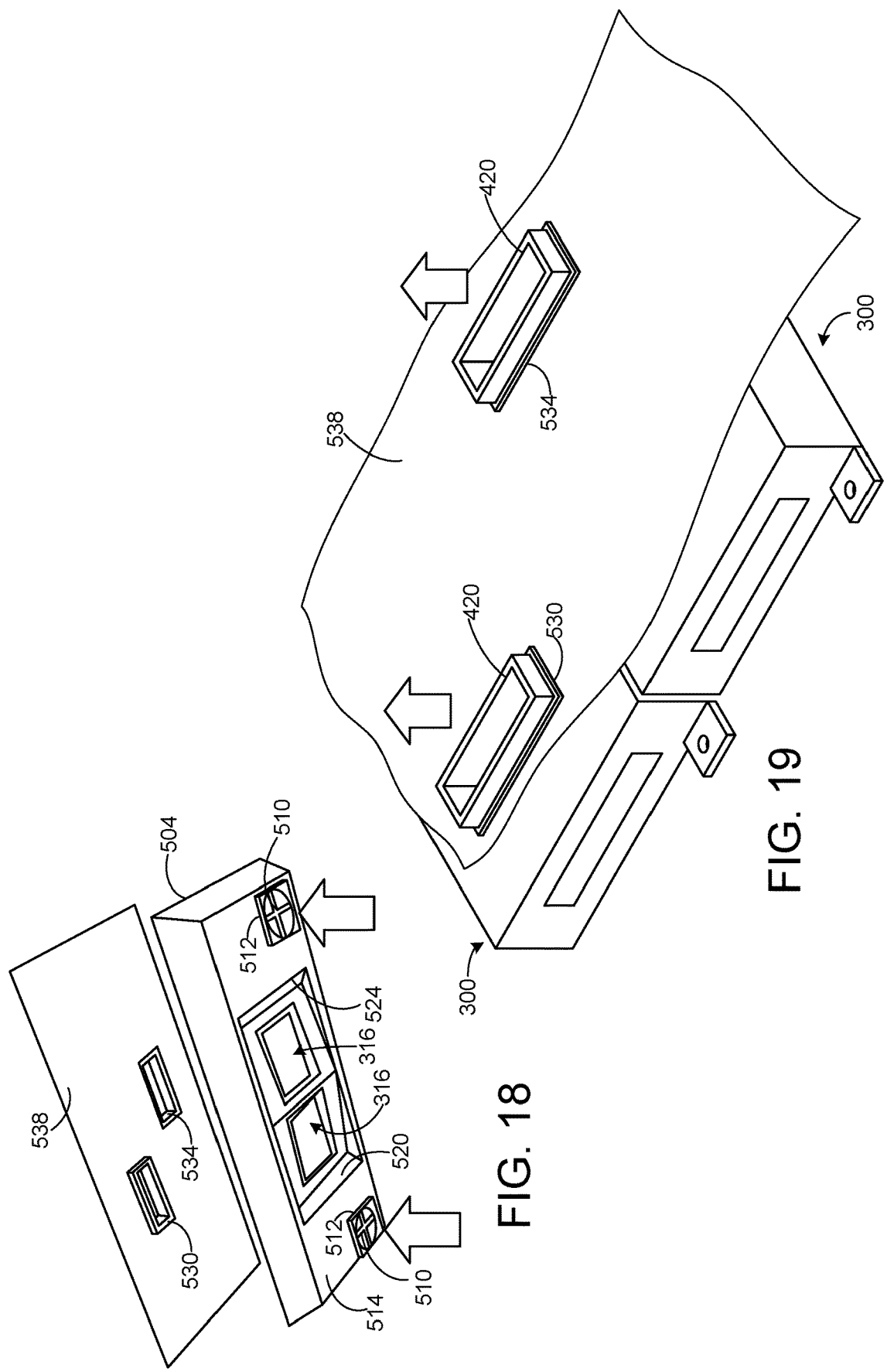

ULTRAVIOLET LIGHT-EMITTING MODULE AND DISINFECTING SYSTEM

CROSS REFERENCE TO RELATED APPLICATIONS

This application claims priority to U.S. Provisional Patent Application Ser. No. 63/124,341, filed Dec. 11, 2020, and to U.S. Provisional Patent Application Ser. No. 63/154,239, filed Feb. 26, 2021, the entirety of which are hereby incorporated herein by reference for all purposes.

FIELD

This disclosure generally relates to disinfecting surfaces, and more particularly to modules, systems and methods that disinfect surfaces using ultraviolet (UV) light.

BACKGROUND

Ultraviolet (UV) light has been used in some settings to disinfect and sanitize surfaces. In some examples, multiple UV emitters are provided in an enclosure and powered by a relatively low power supply, such as 12 watts. While such UV devices offer promise in their ability to render inactive and/or kill certain pathogens, challenges exist in developing devices and systems for more effective delivery of such UV radiation.

SUMMARY

According to one aspect, an ultraviolet (UV) light-emitting module is provided that comprises an enclosure including a rectangular aluminum rear wall comprising a ventilation opening and a rectangular face plate spaced from the rear wall and comprising a light-transmitting aperture. Four aluminum sidewalls extend between the rear wall and the face plate, with at least one sidewall comprising a ventilation opening. At least one fluoropolymer UV light emitter support and a plurality of UV light emitters are within the enclosure. Each of the UV light emitters comprises an elongated lamp that is seated in the fluoropolymer UV light emitter support, with the elongated lamp comprising a first end having a first terminal and an opposing second end having a second terminal. A first lead wire electrically couples the first terminal of each of the elongated lamps to a power source. A second lead wire electrically couples the second terminal of each of the elongated lamps to the power source.

According to another aspect, a system for disinfecting one or more components is provided, with the system comprising a plurality of ultraviolet (UV) light-emitting modules. Each of the modules comprises an enclosure including a rectangular aluminum rear wall comprising a ventilation opening and a rectangular face plate spaced from the rear wall and comprising a light-transmitting aperture. Four aluminum sidewalls extend between the rear wall and the face plate, with at least one sidewall comprising a ventilation opening. At least one fluoropolymer UV light emitter support and a plurality of UV light emitters are within the enclosure. Each of the UV light emitters comprises an elongated lamp that is seated in the fluoropolymer UV light emitter support, with the elongated lamp comprising a first end having a first terminal and an opposing second end having a second terminal. A first lead wire electrically couples the first terminal of each of the elongated lamps to a power source. A second lead wire electrically couples the second terminal of each of the elongated lamps to the power source.

The system further includes a housing that encloses the plurality of UV light-emitting modules. The housing comprises at least one cooling fan that directs air into the housing, and at least one housing ventilation exit opening through which the air escapes.

According to another aspect, a method of assembling a system for disinfecting one or more components is provided. The method is performed using plurality of ultraviolet (UV) light-emitting modules and a housing, wherein each of the UV light-emitting modules includes an enclosure having an aluminum rear wall with a rear wall ventilation opening, a face plate spaced from the rear wall and having a light-transmitting aperture, four aluminum sidewalls extending between the rear wall and the face plate, wherein at least one sidewall of the four aluminum sidewalls comprises a sidewall ventilation opening, and each module further includes at least one fluoropolymer UV light emitter support within the enclosure, a plurality of UV light emitters within the enclosure, wherein each of the UV light emitters comprises an elongated lamp that is seated in the at least one fluoropolymer UV light emitter support, the elongated lamp comprising a first end having a first terminal and an opposing second end having a second terminal, a first lead wire electrically coupling the first terminal of each of the elongated lamps to a power source, and a second lead wire electrically coupling the second terminal of each of the elongated lamps to the power source, and wherein the housing includes at least one cooling fan configured to direct air into the housing and at least a first housing ventilation exit opening and a second housing ventilation exit opening.

The method includes affixing the plurality of UV light-emitting modules inside the housing. The first housing ventilation exit opening is pneumatically coupled to the rear wall ventilation opening of a first UV light-emitting module of the plurality of UV light-emitting modules. The second housing ventilation exit opening is pneumatically coupled to the rear wall ventilation opening of a second UV light-emitting module of the plurality of UV light-emitting modules.

BRIEF DESCRIPTION OF THE DRAWINGS

FIG. 18 shows another exploded view of the housing of FIG. 16.

FIG. 19 shows a partial cutaway view of the cover panel of the housing of FIG. 16.

DETAILED DESCRIPTION

In view of the considerations discussed above, FIGS. 1 and 2 show one example of a system for disinfecting one or more components using ultraviolet (UV) light-emitting modules. As described in more detail below, the system utilizes UV light-emitting modules incorporating one or more cooling features that provide heat transfer functionality to enable the modules to operate at higher power and provide correspondingly higher UV irradiation. In some examples described below, multiple modules are enclosed in a housing that includes one or more cooling fans to circulate air through the modules.

Figure 1:
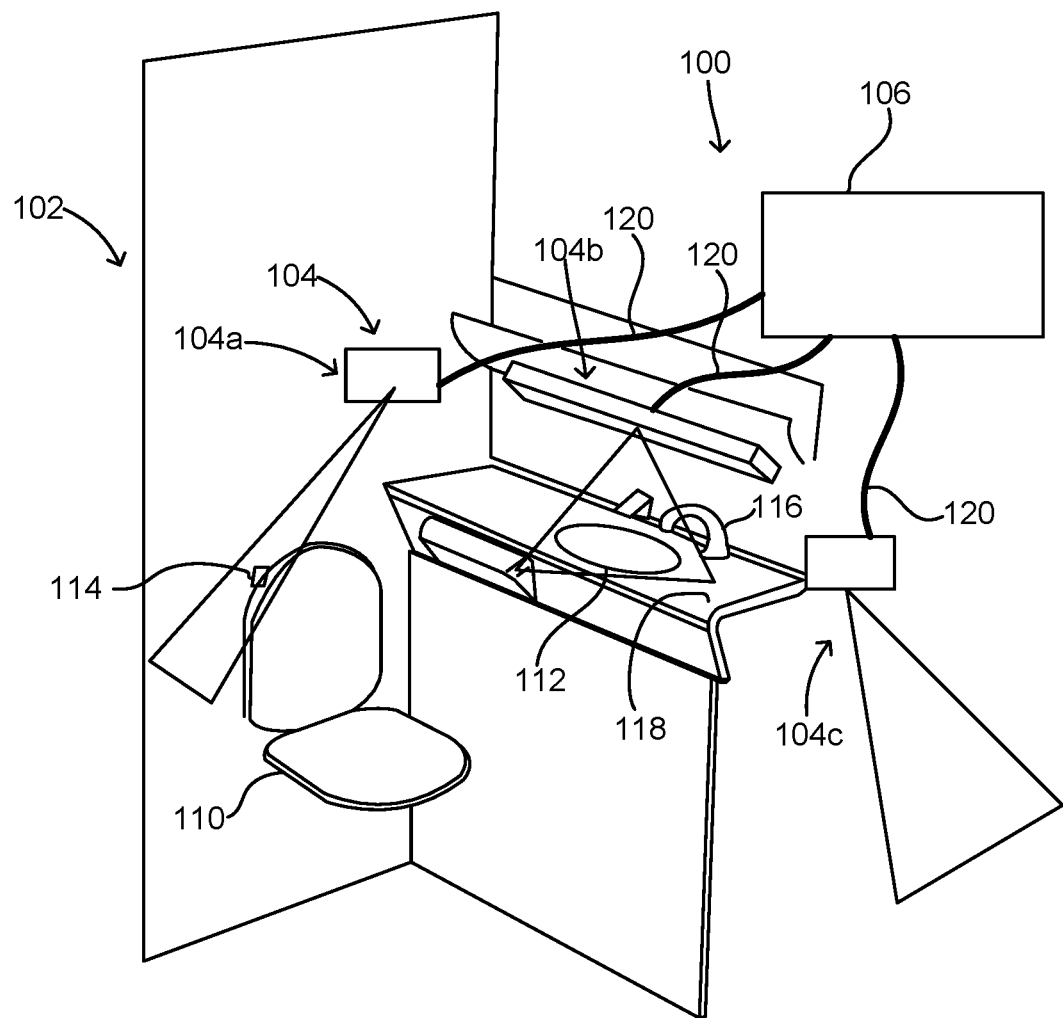
FIG. 1 shows a perspective view of a disinfecting system within a lavatory according to examples of the present disclosure.

FIG. 1 illustrates a perspective view of a lavatory 102 that includes a system 100 for disinfecting one or more components using ultraviolet (UV) light. The system 100 includes a plurality of UV light-emitting modules 104 configured to emit UV light. In different examples, the UV light-emitting modules 104 can take the form of UV light-emitting module 300 shown in FIG. 3 and described in more detail below, or one of the other examples of UV light-emitting modules described herein.

In the example of FIG. 1, three UV light-emitting modules 104a, 104b, and 104c are shown. The system 100 also includes a power supply module 106 that is electrically connected to each of the UV light-emitting modules 104 and provides power to the modules to generate UV light for disinfecting and/or sanitizing components and their surfaces in the lavatory 102.

In other examples, the system 100 utilizes fewer or more than three UV light-emitting modules 104 that are electrically connected to the power supply module 106. In still other examples, the system 100 and/or individually powered UV light-emitting modules 104 can be utilized in a variety of environments, including but not limited to kitchens, galleys, retail establishments, medical facilities, arenas, places of worship, banquet halls, theatres, concert venues, commercial businesses, factories, and other spaces. In some examples, the system 100 and/or individually powered UV light-emitting modules 104 may can be utilized in aircraft, spacecraft, and other vehicles, such as buses, trains, marine vessels, and the like.

Figure 27:
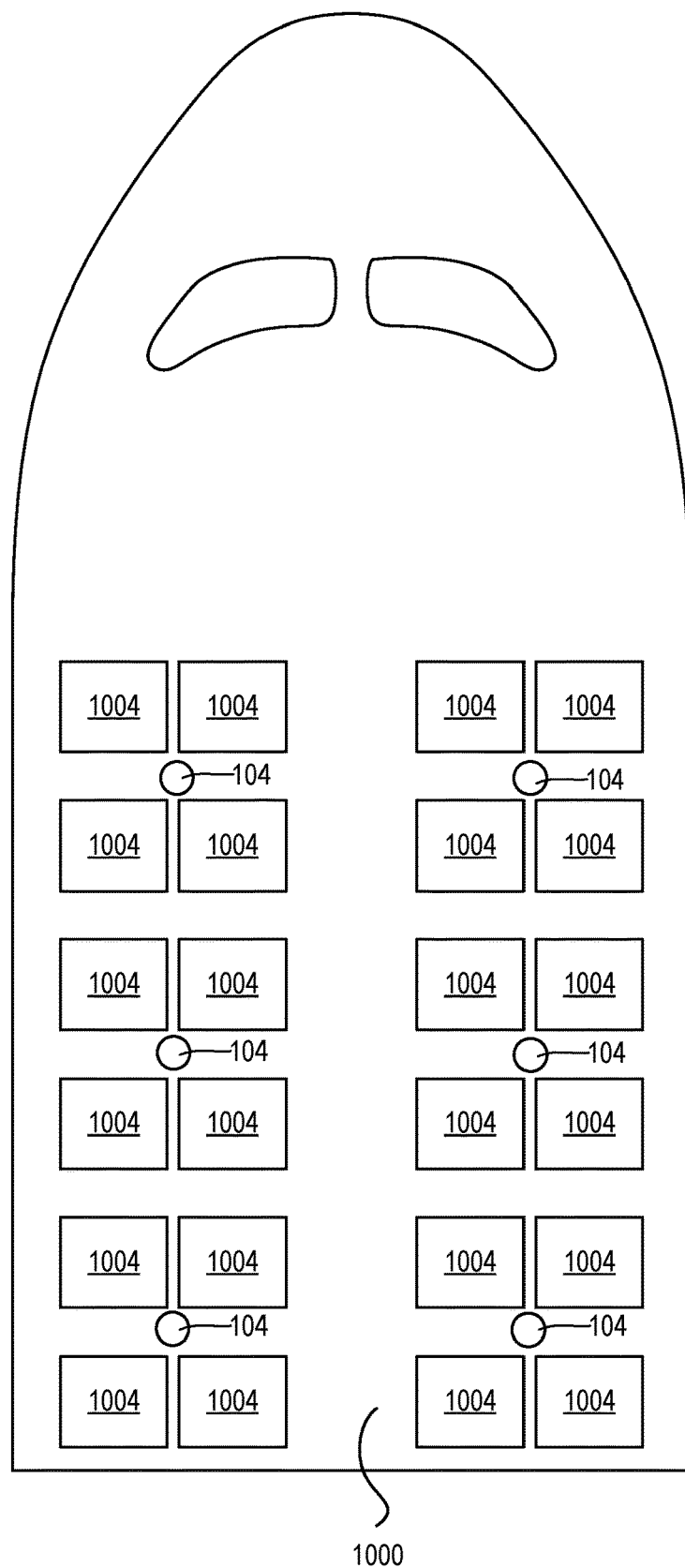
FIG. 27 depicts an aircraft environment in which UV light-emitting modules are installed according to examples of the present disclosure

In a commercial aircraft, the system 100 can be located within a cabin, galley, crew rest area, assembly area, cargo area, flight deck, lavatory, and other areas in which individuals, passengers, flight crew, ground crew, and/or maintenance personnel may be located. In the present example of FIG. 1, the lavatory 102 can be located within a vehicle, such as within a cabin of a commercial aircraft. For example, FIG. 27 depicts an aircraft environment in which UV light-emitting modules 104 are installed above passenger seats 1004 in the cabin 1000 of the aircraft.

In other examples and as described in more detail below, one or more UV light-emitting modules 104 may be utilized in a portable assembly, such as a wand, that is configured to be held by a user. In some examples, such a portable assembly is also configured to be removably mounted to a support structure, such as a wall.

Returning to the example of FIG. 1, the UV light-emitting modules 104 are positioned to emit the UV light towards one or more components within the lavatory 102 for disinfecting and/or sanitizing the components. In the illustrated example, the one or more components include a sink 112 and a toilet 110. In this example, the UV light-emitting modules 104 are positioned to emit UV light towards different components 108. For example, the first UV light-emitting module 104a is positioned to emit UV light towards the toilet 110 including a flush actuator 114 (e.g., lever, button, etc.) of the toilet 110. The second UV light-emitting module 104b is positioned to emit UV light towards the sink 112 and the surrounding region, such as portions of the faucet 116 and countertop 118. The third UV light-emitting module 104c is positioned to emit UV light towards the door (not shown) used to enter and exit the lavatory 102.

In some examples, two or more UV light-emitting modules 104 are positioned to emit UV light towards a common component. In some examples, two or more UV light-emitting modules 104 are physically adjacent and/or mechanically coupled to one another.

The power supply module 106 is electrically connected to the UV light-emitting modules 104 to provide power to the modules. In some examples the power supply module 106 includes processing and/or power modulation circuitry within an enclosure or housing. In different examples the power supply module 106 receives electrical energy from a power source, such as power distribution panel or a battery, and distributes the electrical energy among the UV light-emitting modules 104.

In the example of FIG. 1, the power supply module 106 is mounted within the lavatory 102 and is electrically connected to the UV light-emitting modules 104 via respective power leads 120, such as one or more electrical wires or power cables. In other examples, one or more of the UV light-emitting modules 104 are integrated with the power supply module 106 in a common housing.

As described in more detail below, in some examples a UV light-emitting module 104 utilizes a small form factor to provide improved aesthetics by occupying less space. The smaller form factor also can enable the location of the UV light-emitting modules 104 closer to the components to be disinfected as compared to larger form factor UV light emitters. For example, the smaller UV light-emitting modules 104 can be inconspicuously mounted behind or within structures that would not be possible for larger UV light emitters. In one potential advantage of the present disclosure, locating the UV light-emitting modules 104 closer to components increases the radiant flux (irradiance) provided to surfaces of the components. In this manner, by locating the UV light-emitting modules 104 closer to the components 108 as compared to larger UV light emitters, a designated UV dosage can be provided to the components utilizing less energy and/or in a shorter length of time as compared to the same dosage applied by larger UV light-emitting modules.

Figure 2:
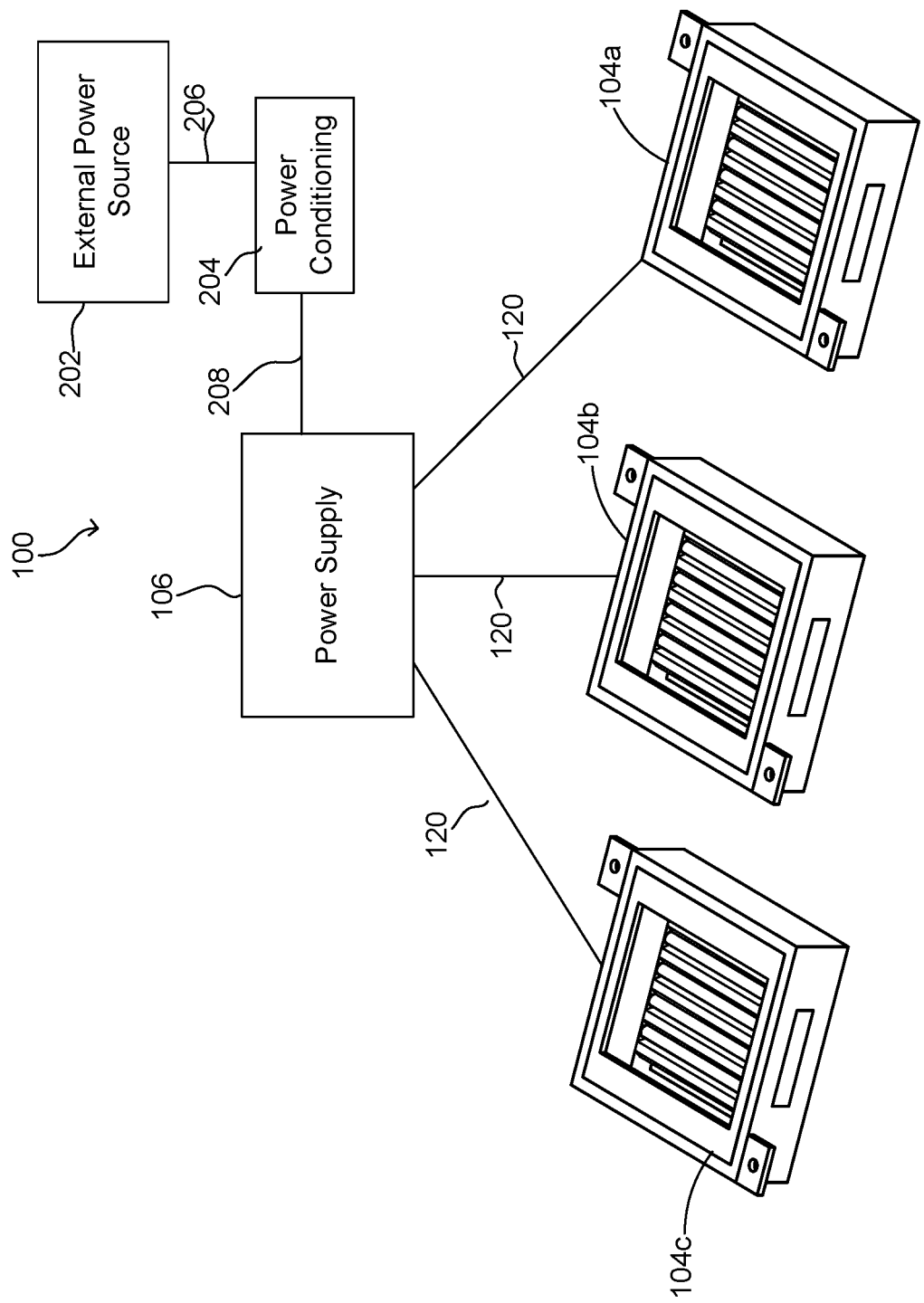
FIG. 2 shows a schematic diagram of the disinfecting system of FIG. 1 according examples of the present disclosure.

FIG. 2 illustrates a schematic block diagram of the system 100 according to an example of the present disclosure. In this example, the power supply module 106 receives electrical energy from an external power source 202 that is separate and discrete from the power supply module 106. In some examples the power source 202 is a vehicle electrical system onboard a vehicle or an electrical system of a building or facility. In other examples, the power source 202 is a battery, a generator, or the like.

In the present example the power supply module 106 is electrically connected to the external power source 202 via a power conditioning circuit 204 and power cables 206 and 208. In different examples the power conditioning circuit 204 includes one or more rectifiers, power factor correction circuits, and/or capacitors for electromagnetic interference filtering. In other examples, the power conditioning circuit 204 is integrated with the power supply module 106 in a common enclosure, such as a housing of the power supply module.

In this example, the power supply module 106 receives electrical energy from the power conditioning circuit 204 and controls distribution of the electrical energy among the UV light-emitting modules 104. In this example, the power conditioning circuit 204 receives alternating current (AC) electrical energy from the external power source 202 and converts the AC electrical energy to DC electrical energy. This DC electrical energy is supplied to the power supply module 106, which converts the DC electrical energy to AC electrical energy and supplies the AC to the UV light-emitting modules 104 to power the generation of UV light as described in more detail below. In some examples, the power supply module 106 also controls one or more operations of the UV light-emitting modules 104, such as activating and deactivating the modules, and modulating the power output of the modules.

As described in more detail below, UV light-emitting modules of the present disclosure utilize one or more cooling features that enable the modules to operate at higher power and provide correspondingly higher UV irradiation than prior UV emitters. Additionally and in some examples described below, multiple modules are enclosed in a housing that includes one or more cooling fans to circulate air through the module(s).

Figure 3:
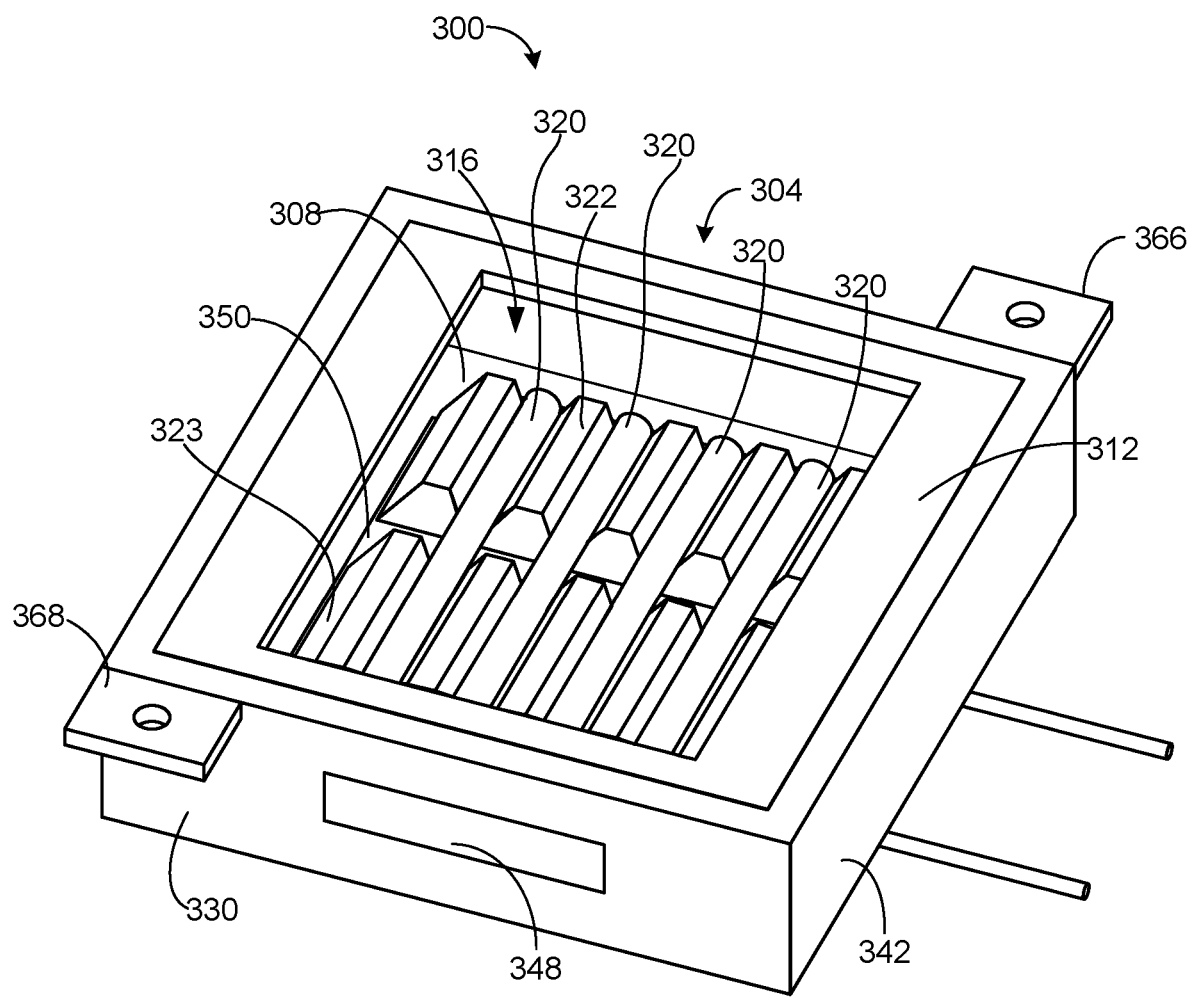
FIG. 3 shows one example of an ultraviolet (UV) light-emitting module according to examples of the present disclosure.
Figure 4:
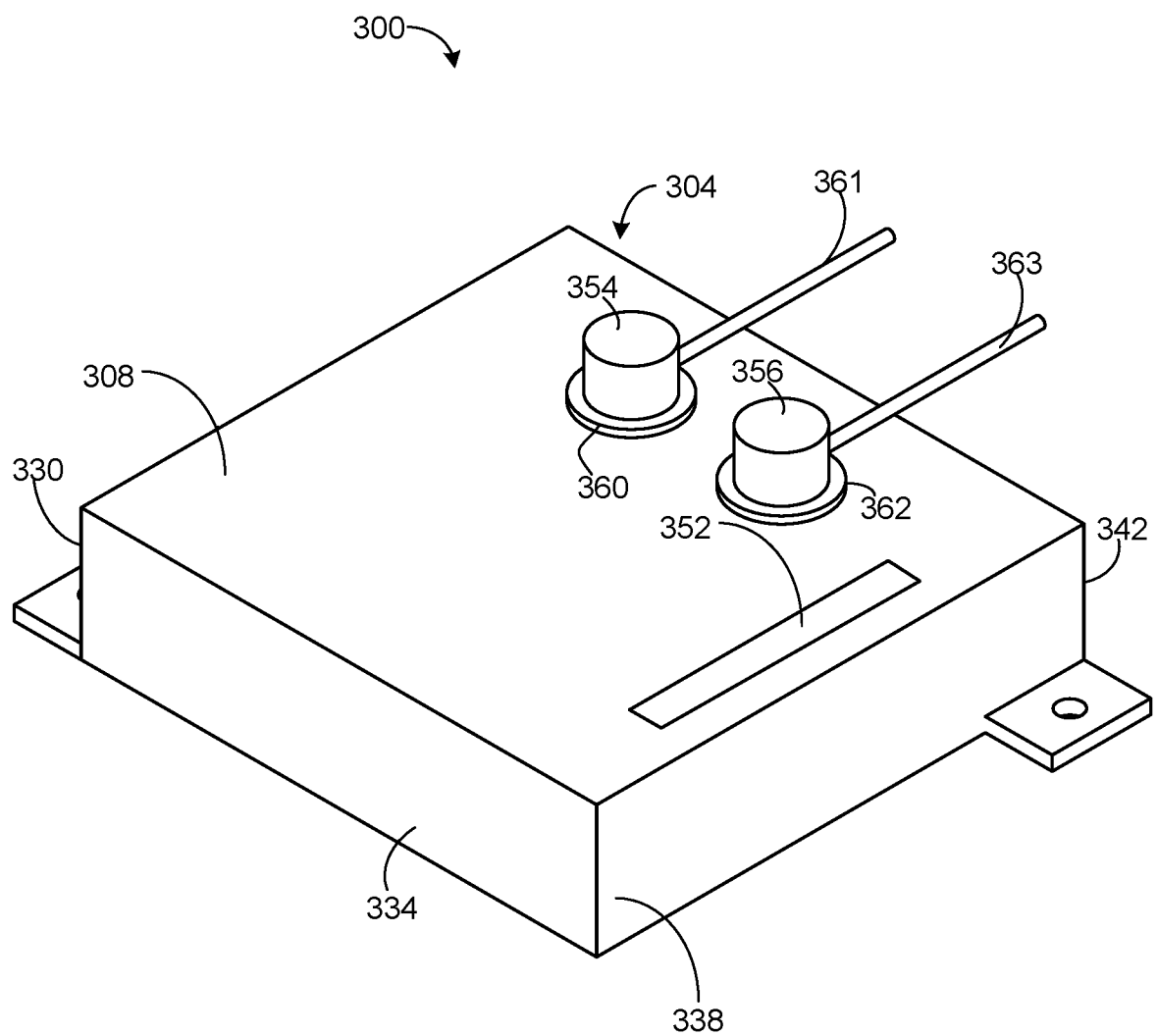
FIG. 4 shows another view of the UV light-emitting module of FIG. 3.
Figure 5:
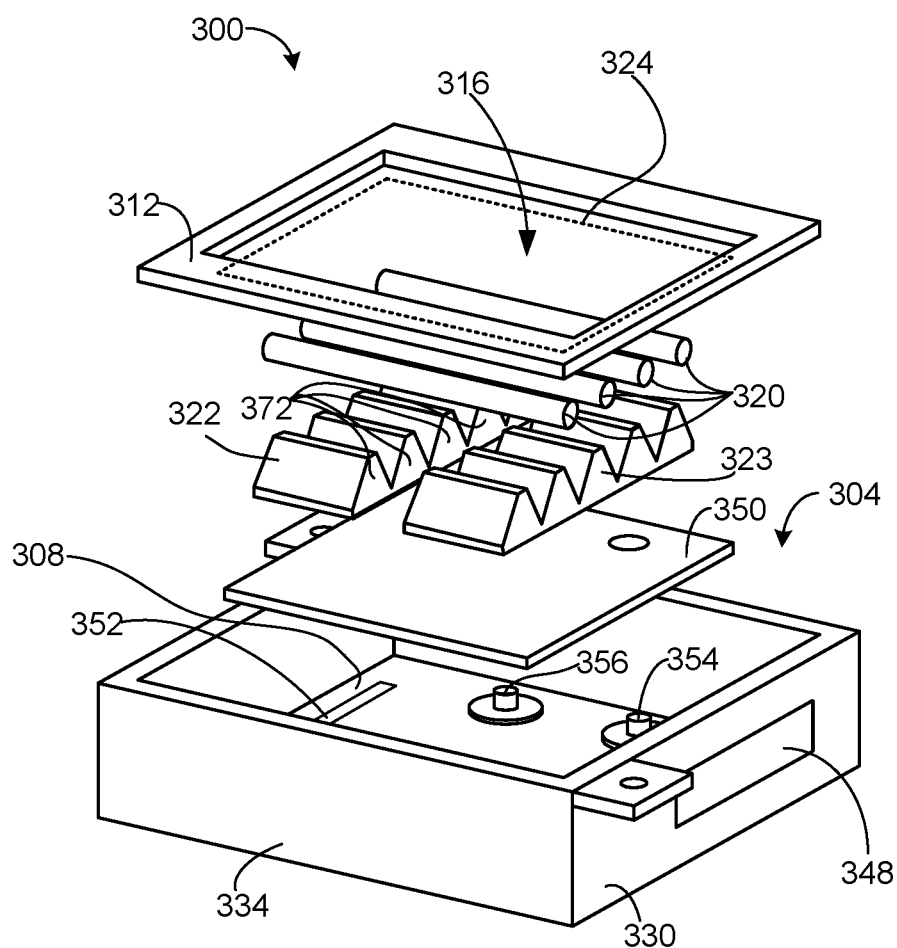
FIG. 5 shows an exploded view of the UV light-emitting module of FIG. 3.

With reference now to FIGS. 3-5, one example of a UV light-emitting module 300 according to the present disclosure is illustrated. In different use case examples, the UV light-emitting modules 104 described above may take the form of UV light-emitting module 300 shown in FIGS. 3-5 or one of the other examples of UV light-emitting modules described further below. In different use cases, the UV light-emitting module 300 and the other examples of UV light-emitting modules described herein can be utilized in a UV disinfecting system, such as system 100, and/or as standalone devices.

In the example of FIGS. 3-5, the UV light-emitting module 300 comprises an enclosure 304 that includes a rear wall 308 and a face plate 312 spaced from the rear wall 308. The face plate 312 includes a light-transmitting aperture 316 through which UV light from one or more UV light emitters within the enclosure is transmitted. In this example, the UV light-emitting module 300 utilizes four UV light emitters 320. In other examples, fewer or more than four UV light emitters may be utilized in UV light-emitting modules according to the present disclosure.

In some examples, the UV light emitters 320 can be excimer lamps that utilize a krypton-chlorine (Kr—Cl) gas mixture provided in the lamp bulb. Such excimer lamps emit UV light having a wavelength of 222 nm that can disinfect and sanitize component surfaces via localized anti-viral and antimicrobial effects. Further, 222 nm UV light can disinfect and sanitize surfaces without skin damaging effects associated with conventional germicidal ultraviolet (UV) exposure. In other examples, the UV light-emitting module 300 can utilized other types of UV emitters and UV lamps. Additionally and as described in more detail below, the UV light emitters 320 are seated in one or more UV light emitter supports within the enclosure 304.

In the present example and as shown in FIG. 5, a low pass filter 324 is located adjacent to the light-transmitting aperture 316 of the face plate 312. The low pass filter 324 can be used to remove or filter out substantially all light emissions generated by the UV light emitters 320 except for 222 nm wavelength ultraviolet light.

In this example the enclosure 304 has a rectangular shape formed by a first sidewall 330, second sidewall 334, third sidewall 338 and fourth sidewall 342. Each of the sidewalls extends between the rear wall 308 and the face plate 312. In other examples, other enclosures of the present disclosure can have other shapes and form factors, such as a circular enclosure formed by a single circular sidewall.

As noted above, and in one potential advantage of the present disclosure, the enclosure 304 utilizes one or more cooling features that enable the module 300 to operate at higher power and provide correspondingly higher UV irradiation than prior UV emitters. In this example, the enclosure includes cooling features in the form of a sidewall ventilation opening 348 in first sidewall 330 and a rear wall ventilation opening 352 in the rear wall 308. In this manner, these ventilation openings enable airflow through the interior of the enclosure 304 and over the surfaces of the UV light emitters 320, to thereby cool the emitters by transferring heat generated by emitters from the enclosure. As described below, in other examples ventilation openings can be provided in other locations on the enclosure 304.

In some examples, the rear wall 308 and the first sidewall 330, second sidewall 334, third sidewall 338 and fourth sidewall 342 of the enclosure 304 are fabricated from a plastic material. In other examples, the rear wall 308 and the first sidewall 330, second sidewall 334, third sidewall 338 and fourth sidewall 342 are fabricated from aluminum. Advantageously and in these examples, the aluminum walls have a higher thermal conductivity than plastic, thereby providing greater heat transfer and dissipation from the UV light emitters 320 through the walls of the enclosure 304.

In some examples in which the rear wall 308 and four sidewalls 330, 334, 338 and 342 are fabricated from aluminum, the face plate 312 is fabricated from plastic. In other examples, the face plate 312 is also fabricated from aluminum to provide even greater heat transfer from within the enclosure 304.

As noted above, in the example of FIGS. 3-5 the UV light emitters 320 are seated in V-shaped grooves in a first UV light emitter support 322 and a second UV light emitter support 323 that extend parallel to one another. In some examples where the rear wall 308 and four sidewalls 330, 334, 338 and 342 are fabricated from aluminum, the UV light emitter supports 322, 323 are also fabricated from a conductive material, such as aluminum. In this manner and by seating the UV light emitters 320 in the supports, the emitters are electrically coupled to the supports. In other examples and as described in more detail below, the UV light emitter supports 322, 323 are fabricated from a fluoropolymer and the UV light emitters 320 are electrically coupled to a power source via lead wires.

In the example of FIGS. 3-5, where the UV light emitter supports 322, 323 and the rear wall 308 are aluminum, a thermally conductive and electrically insulating separator 350 is positioned between the UV light emitter supports and the rear wall to electrically isolate the UV light emitter supports from the aluminum rear wall. In some examples, the thermally conductive and electrically insulating separator 350 has a thermal conductivity of approximately 15 international British thermal unit per hour per square foot per degree Fahrenheit (BTU)/(° F. Hr. Ft.$^2$) or higher. In one example, the thermally conductive and electrically insulating separator 350 is fabricated from an alumina-based ceramic. For example, the thermally conductive and electrically insulating separator 350 can be fabricated from Cotronics Durapot 810 castable ceramic cement, manufactured by Cotronics Corporation. Accordingly, in these examples the higher thermal conductivity of separator 350 further facilitates heat transfer from the enclosure to cool the UV light emitters 320.

With reference to FIGS. 4 and 5, the first UV light emitter support 322 and second UV light emitter support 323 receive power via first electrical conductor 354 and second electrical conductor 356, respectively, that extend through the rear wall 308 into the UV light emitter supports. In this example, the first electrical conductor 354 and second electrical conductor 356 also extend through apertures in the thermally conductive and electrically insulating separator 350.

The first electrical conductor 354 and second electrical conductor 356 are electrically coupled to a power source via wires 361, 363. In some examples the power source is the power supply module 106 of system 100. The first electrical conductor 354 is electrically insulated from the rear wall 308 by a first electrically insulating bushing 360 between the first electrical conductor and the rear wall. Similarly, the second electrical conductor 356 is electrically insulated from the rear wall 308 by a second electrically insulating bushing 362 between the first electrical conductor and the rear wall.

In some examples, the enclosure 304 includes attachment tabs 366 and 368 configured to receive a fastener for securing the enclosure to a surface.

Figure 6:
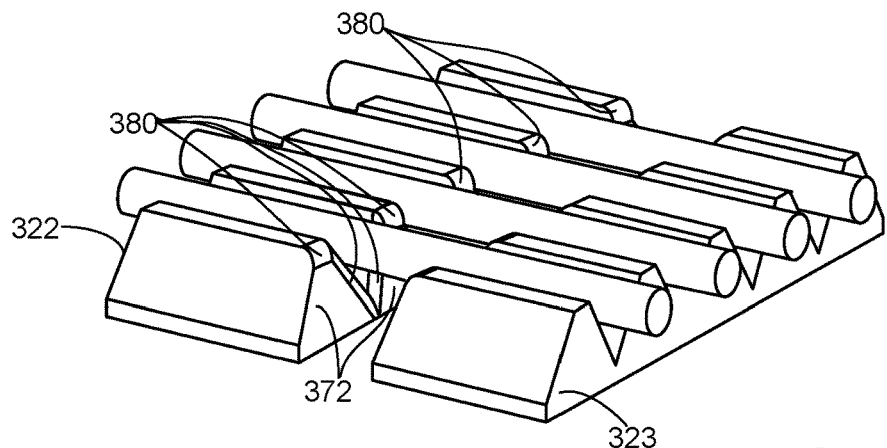
FIG. 6 shows a plurality of triangular-shaped internal support surfaces that include radiused edges according to examples of the present disclosure.
Figure 7:
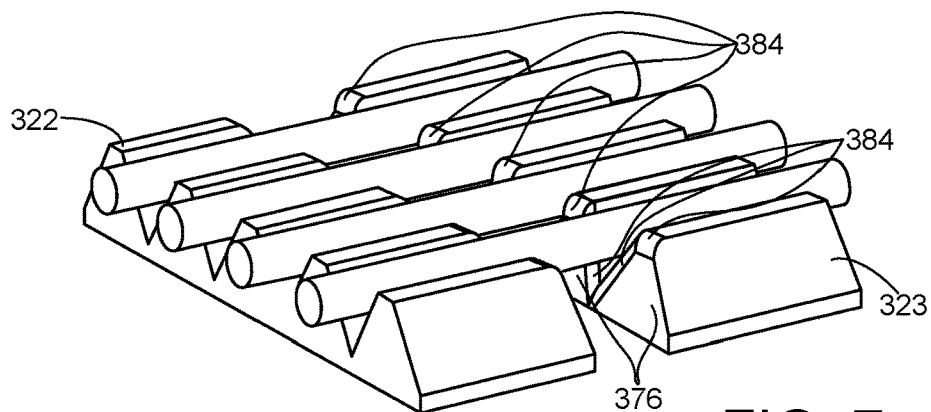
FIG. 7 shows another view of the plurality of triangular-shaped internal support surfaces of FIG. 6.
Figure 8:
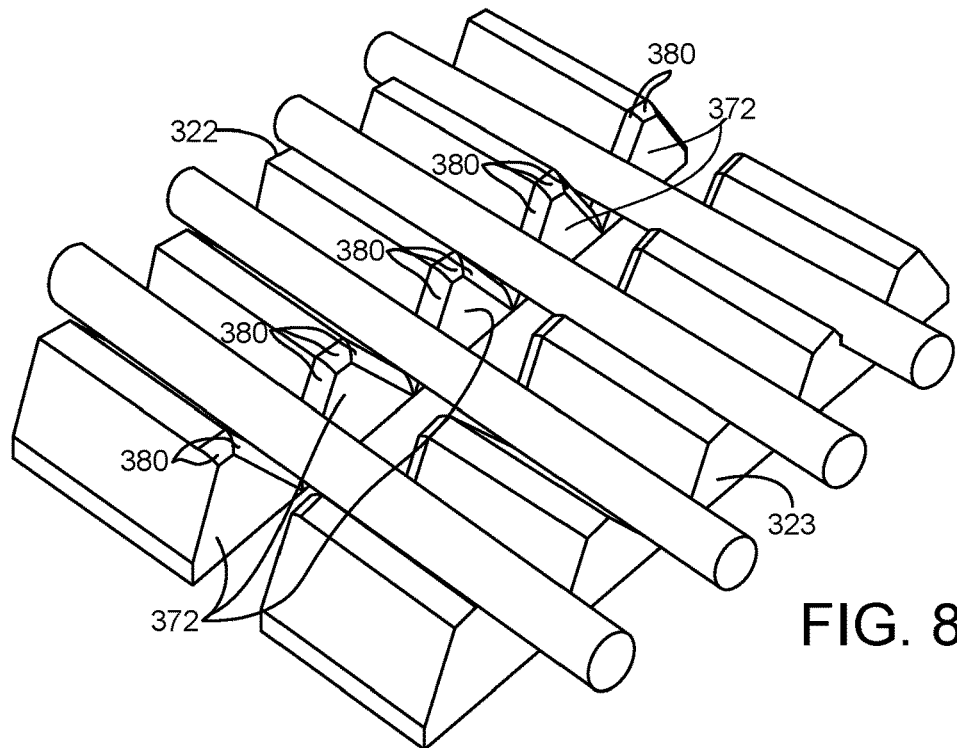
FIG. 8 shows another view of the plurality of triangular-shaped internal support surfaces of FIG. 6.

With reference now to FIGS. 5-8, the first UV light emitter support 322 comprises a plurality of first triangular-shaped internal support surfaces 372 that are facing corresponding second triangular-shaped internal support surfaces 376 of the second UV light emitter support 323. In some examples and as shown in FIGS. 6-8, each of the first triangular-shaped internal support surfaces 372 includes first radiused edges 380 along one or both upwardly extending sides and the apex. Similarly, each of the second triangular-shaped internal support surfaces 376 includes second radiused edges 384 along one or both upwardly extending sides and the apex. In some examples, these radiused edges can have a radius of between approximately 0.05 inches and 0.10 inches. Advantageously in these examples, by providing the radiused edges on the first and second triangular-shaped internal support surfaces 372, 376 that face each other, a likelihood of electrical arcing between the first internal support surfaces 372 and the second internal support surfaces 376 is reduced.

Figure 9:
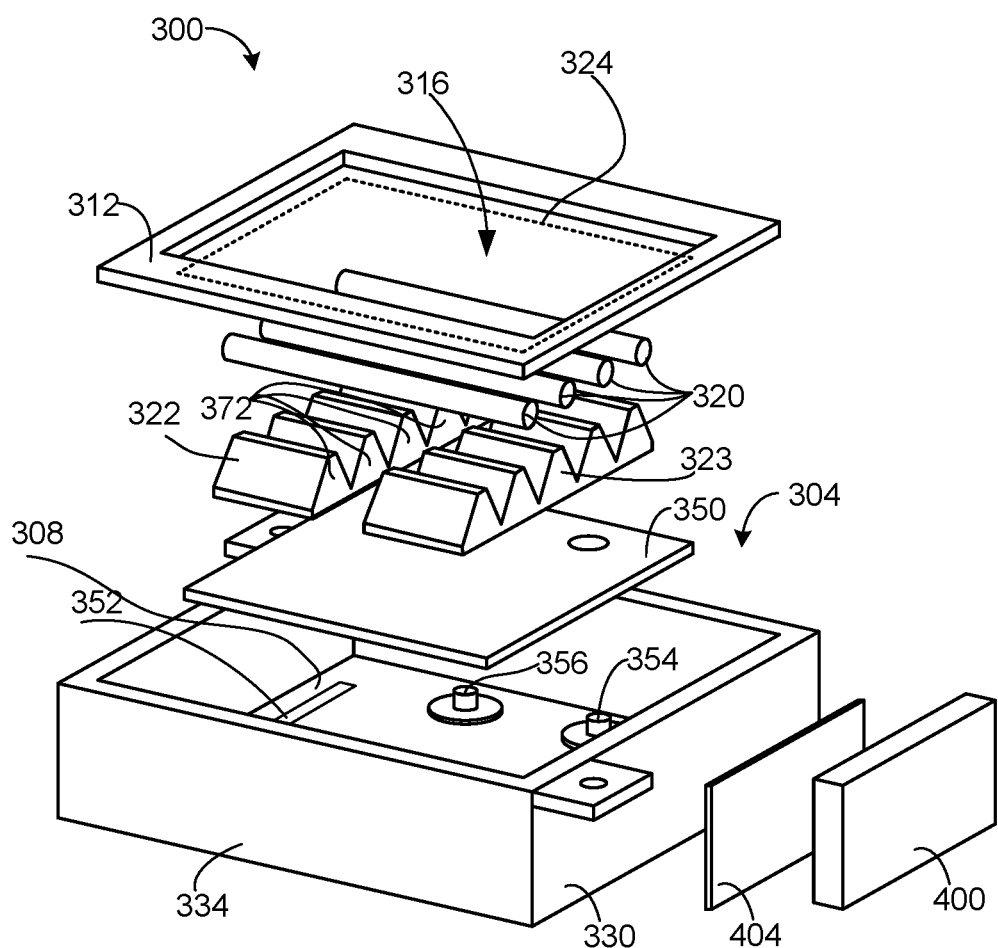
FIG. 9 shows an exploded view of another example of an ultraviolet (UV) light-emitting module including a circuit board according to examples of the present disclosure.

With reference now to FIG. 9, in some examples the UV light-emitting module 300 also includes a circuit board 400 comprising a UV LED that is configured to pre-ionize gas in the UV light emitters 320. In some examples where the first sidewall 330 is a conductive material, such as aluminum, an electrical insulator panel 404 is provided between the circuit board 400 and the first sidewall 330.

Figure 10:
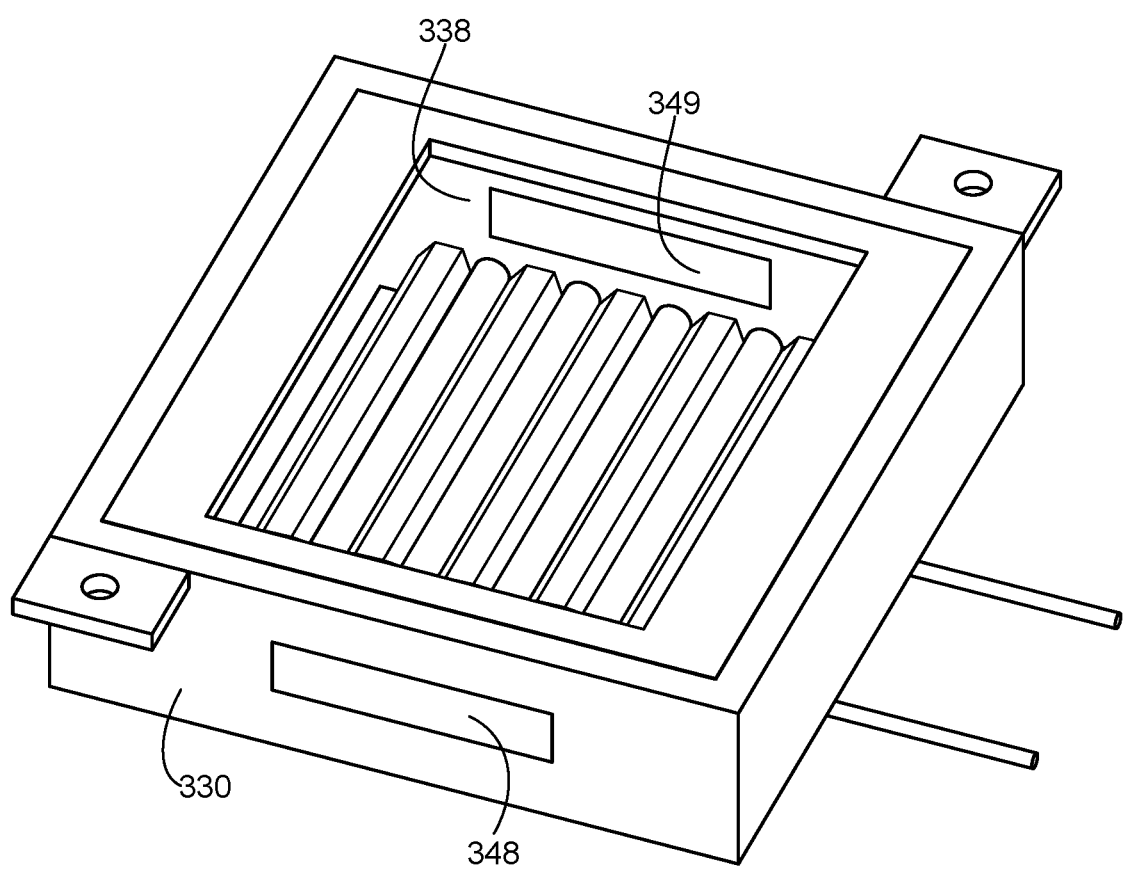
FIG. 10 shows another example of an ultraviolet (UV) light-emitting module including two sidewall ventilation openings according to examples of the present disclosure.
Figure 11:
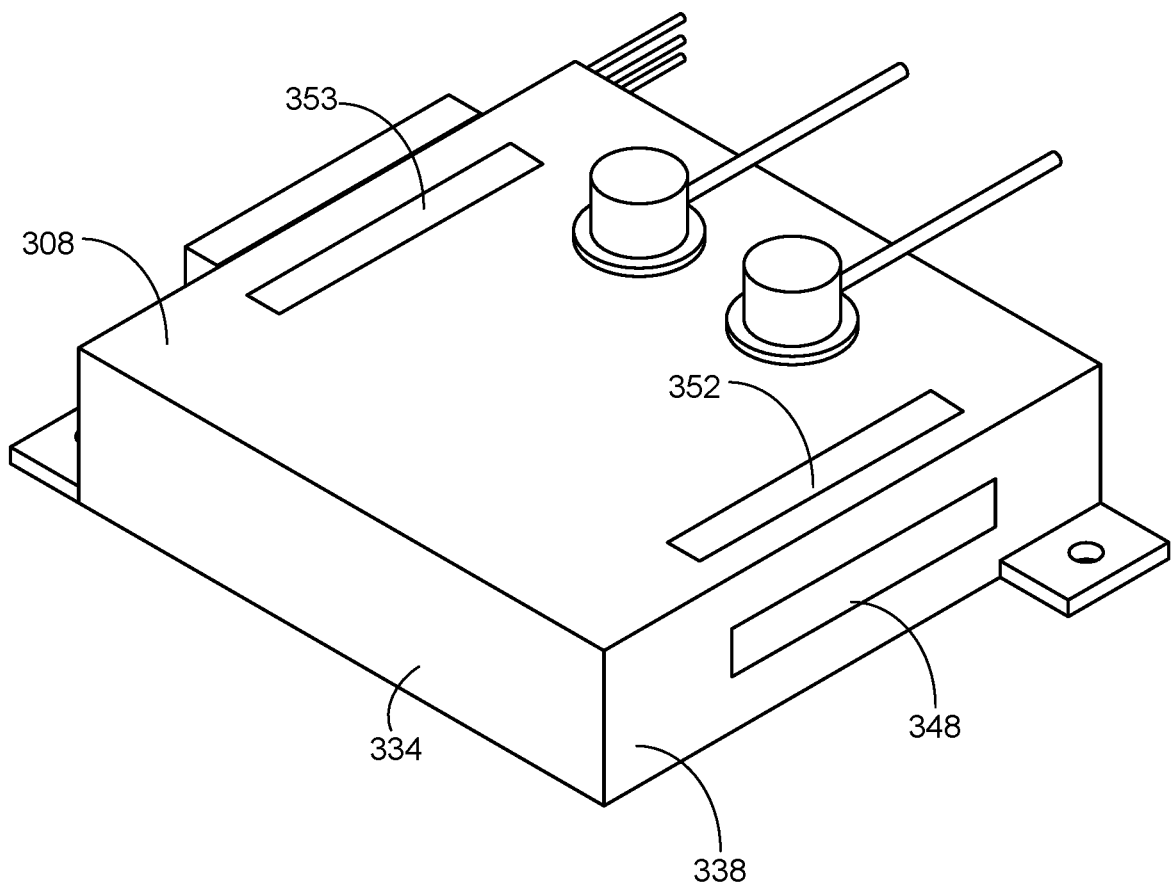
FIG. 11 shows another example of an ultraviolet (UV) light-emitting module including two rear wall ventilation openings and a sidewall ventilation opening according to examples of the present disclosure.

As noted above, in other examples one or more ventilation openings can be provided in two or more of the four sidewalls of the enclosure 304. For example and with reference to FIG. 10, in this example the enclosure includes a first sidewall ventilation opening 348 in first sidewall 330 and a second sidewall ventilation opening 349 in third sidewall 338. In a similar manner and in various examples, the rear wall 308 can include two or more ventilation openings. For example and with reference to FIG. 11, in this example the enclosure includes a first rear wall ventilation opening 352 and a second rear wall ventilation opening 353 in rear wall 308. Additionally, in this example a sidewall ventilation opening 348 in third sidewall 338 is provided.

In other examples of enclosures according to the present disclosure, ventilation openings of any suitable combination, quantity, size and/or shape can be provided in one or more of the sidewalls and in the rear wall 308.

Figure 12:
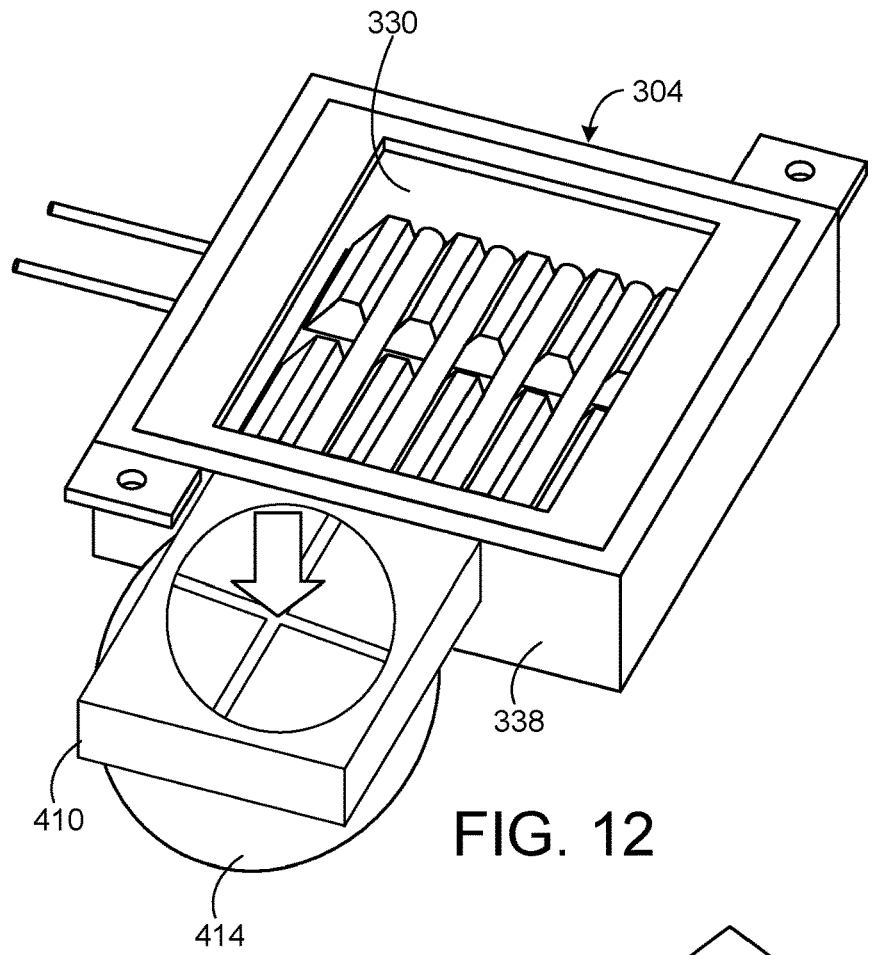
FIG. 12 shows another example of an ultraviolet (UV) light-emitting module including a cooling fan according to examples of the present disclosure.

In some examples, the module 300 may include a cooling fan configured to deliver forced air through either a sidewall ventilation opening or a rear wall ventilation opening. For example and with reference to FIGS. 12 and 13, a cooling fan 410 is mounted to third sidewall 338 adjacent to ducting 414 that directs air from the fan into ventilation opening 349 in third sidewall 338. The air passes over and through the UV light emitters 320 and other components inside the enclosure 304 and exits through rear wall ventilation opening 352 in rear wall 308. In this example a fitting 420 is affixed to the rear wall ventilation opening 352 to direct the exiting airflow away from the module.

Figure 14:
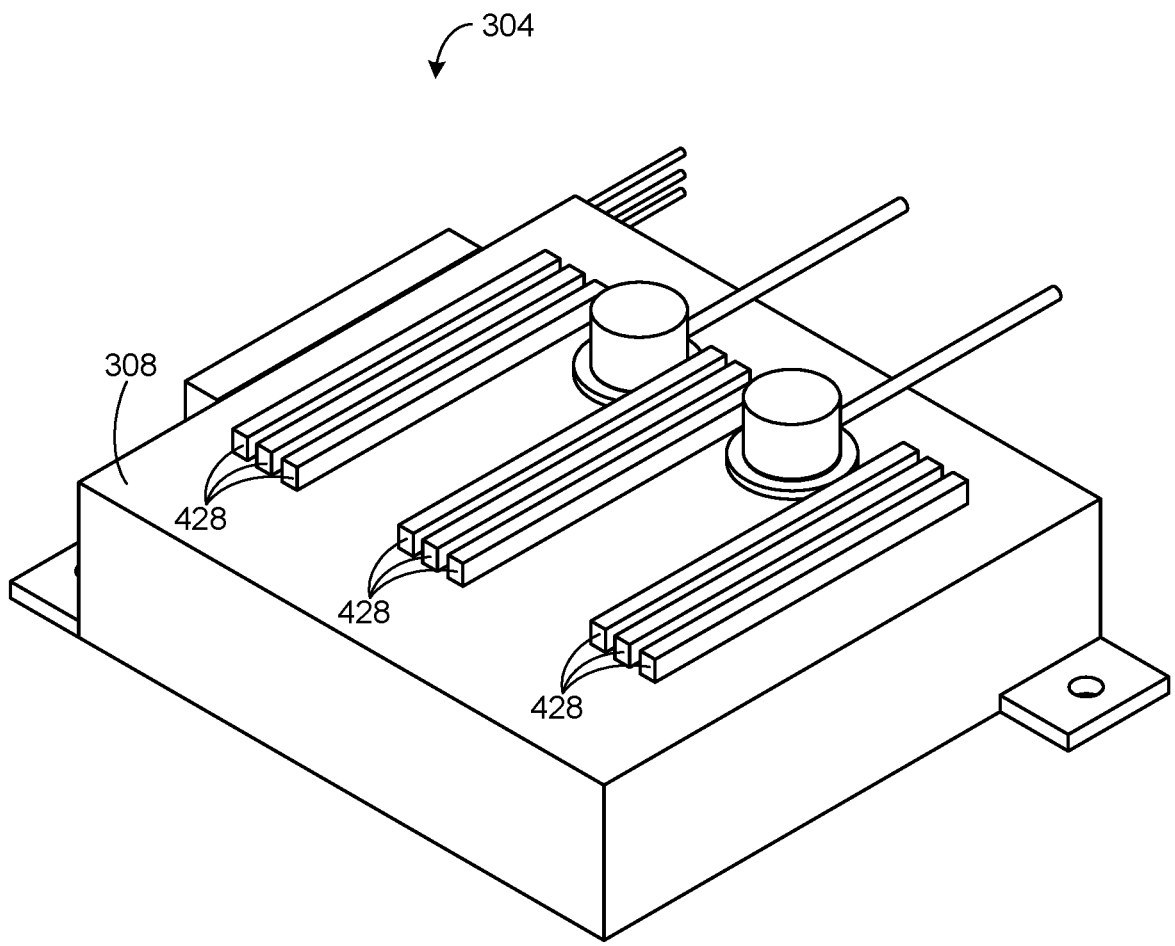
FIG. 14 shows another example of an ultraviolet (UV) light-emitting module including a heat sink feature and according to examples of the present disclosure.

With reference now to FIG. 14, in some examples the enclosure 304 is pneumatically sealed to contain off-gases that may be generated by the UV light emitters 320. In this example, the enclosure contains no ventilation openings and is pneumatically sealed to prevent any off-gasses from escaping to atmosphere.

In some examples, UV light-emitting modules of the present disclosure include one or more cooling features in the form of a heat sink feature. With continued reference to FIG. 14, in this example the module includes a heat sink feature in the form of a plurality of fins 428 extending from the rear wall 308. In different examples the fins may have different sizes and shapes, such as thin elongated plates arranged adjacent to one another. The number and placement of the fins on the enclosure also can vary according to applications and use environments. For example, heat sink fins can additionally or alternatively be located on one or more sidewalls of the enclosure.

Figure 15:
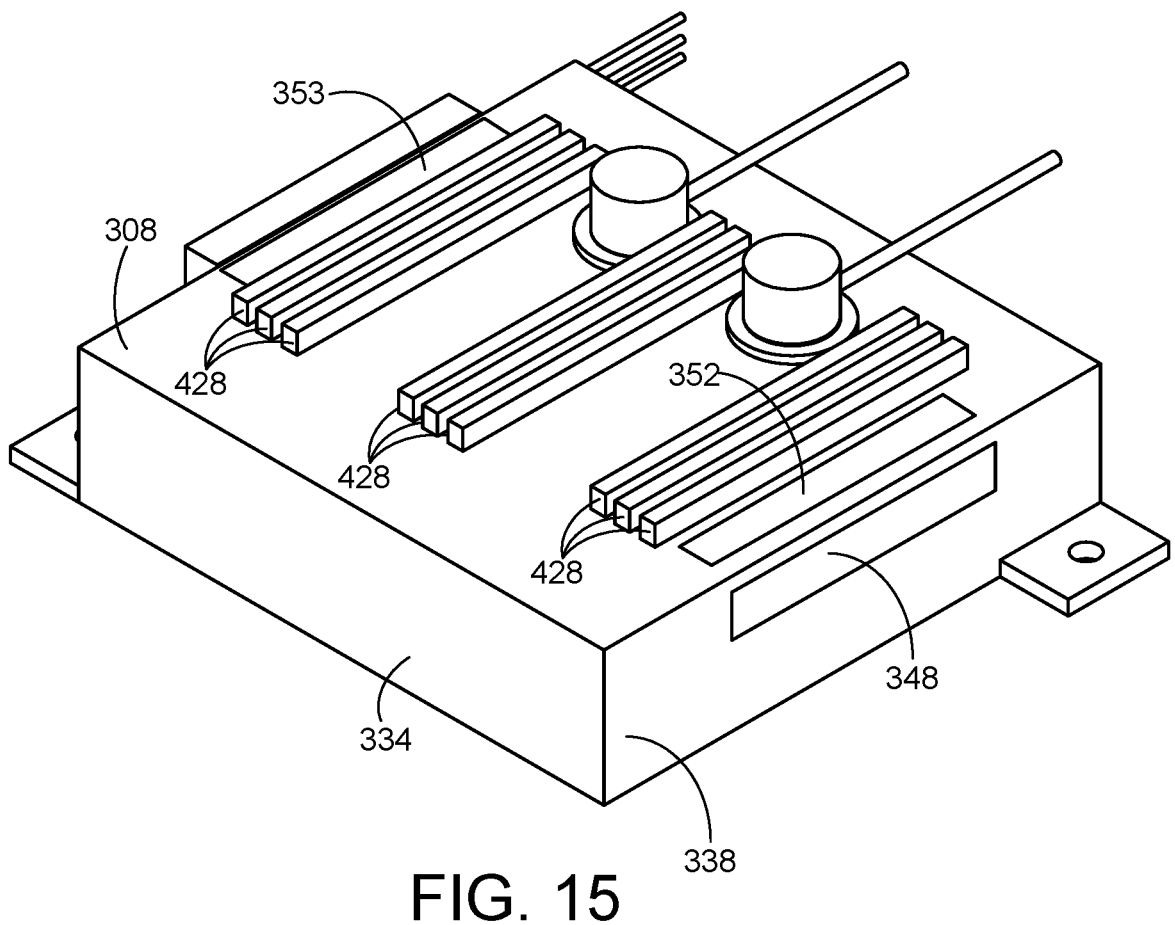
FIG. 15 shows another example of an ultraviolet (UV) light-emitting module including a heat sink feature and a plurality of ventilation openings according to examples of the present disclosure.
Figure 16:
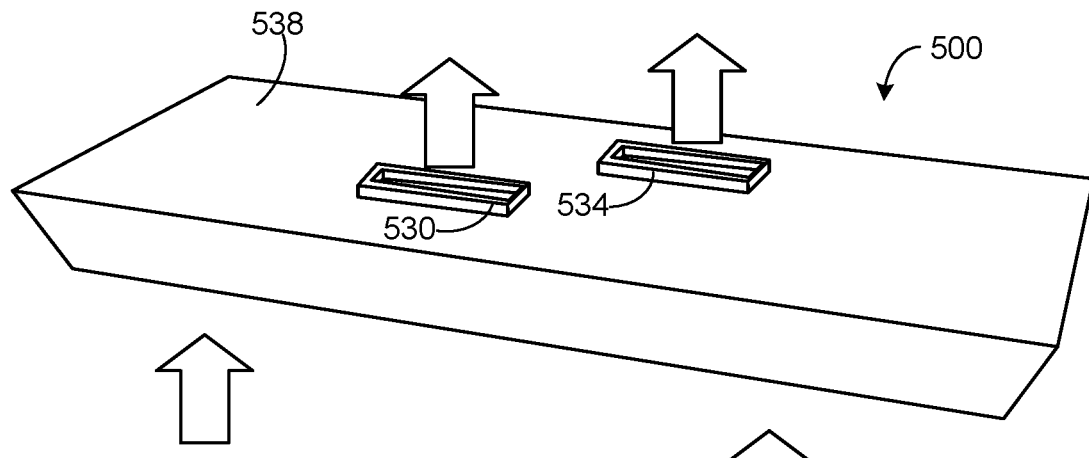
FIG. 16 shows an example of a housing for two ultraviolet (UV) light-emitting modules according to examples of the present disclosure.

In some examples, modules according to the present disclosure can include one or more ventilation openings and one or more heat sink features. For example and with reference to FIG. 15, in this example the module includes the plurality of fins 428 extending from the rear wall 308, a first rear wall ventilation opening 352 and a second rear wall ventilation opening 353 in rear wall 308, and a sidewall ventilation opening 348 in third sidewall 338.

In some examples, one or more UV light-emitting modules 300 are enclosed in a housing that provides forced ventilation via at least one cooling fan that directs air into the housing and at least one housing ventilation exit opening through which the air escapes. With reference now to FIGS. 16-19, in one example a housing 500 includes a container portion 504 in which two UV light-emitting modules 300 according to the present disclosure are located. Both UV light-emitting modules 300 include a single sidewall ventilation opening 349 and a single rear wall ventilation opening to which a fitting 420 is affixed.

As shown in FIG. 18, the container portion 504 includes two intake cooling fans 510 configured to pull air into and pressurize the housing 500. Each of the cooling fans 510 are seated within and pneumatically coupled to a respective housing ventilation intake opening 512 in the housing 500. A bottom panel 514 of the container portion 504 includes module cutouts 520, 524 in which the two UV light-emitting modules 300 are seated. The light-transmitting apertures 316 in each of the modules 300 face downwardly through the cutouts 520, 524 to direct UV light downwardly from the housing 500.

Figure 13:
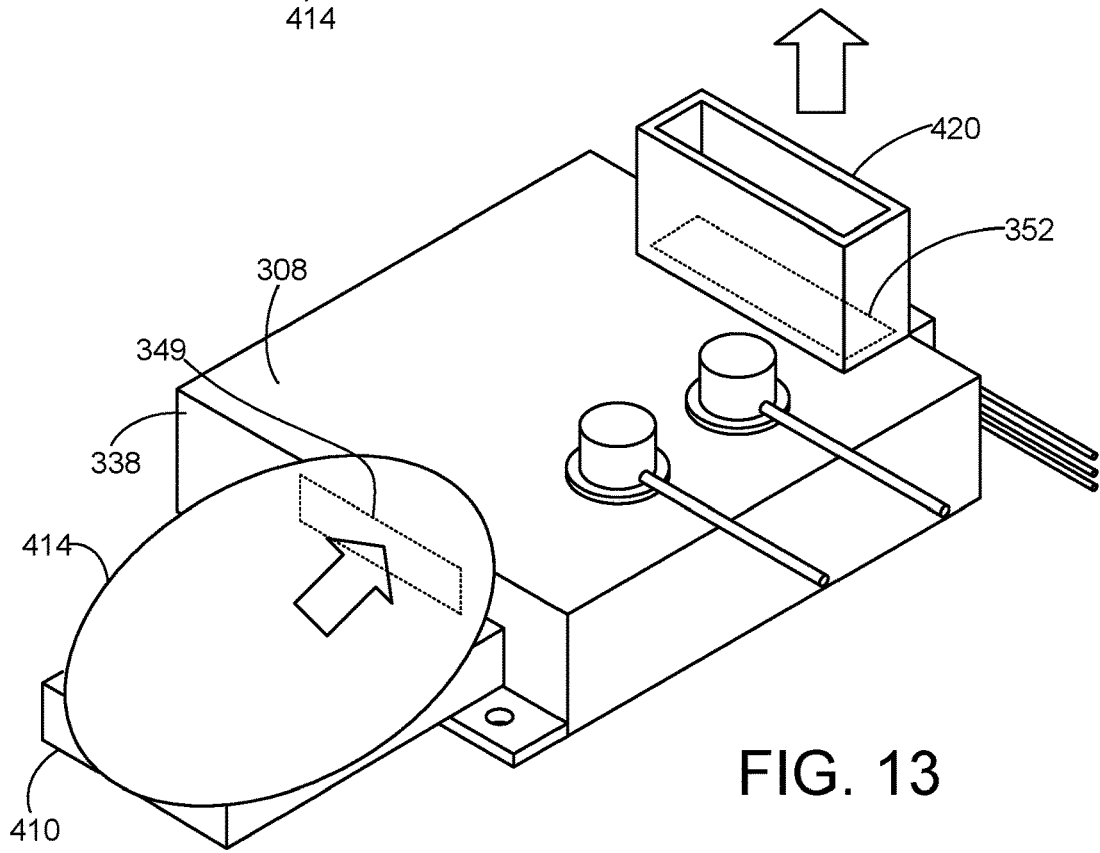
FIG. 13 shows another view of the UV light-emitting module of FIG. 12.
Figure 17:
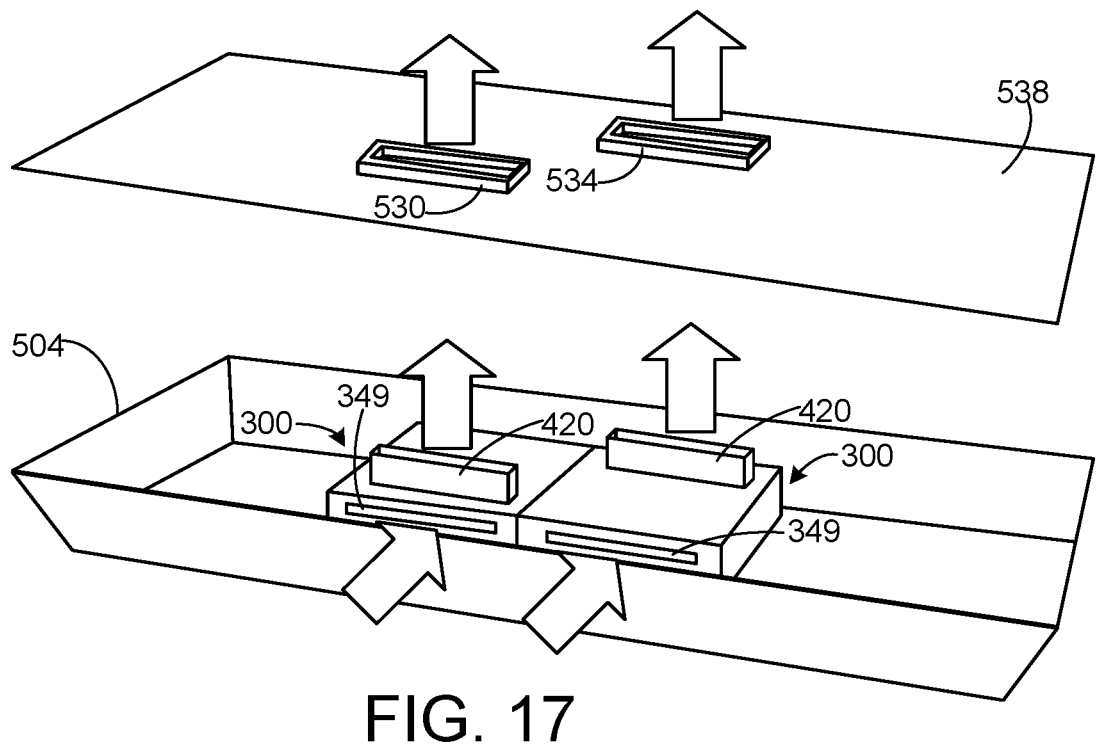
FIG. 17 shows an exploded view of the housing of FIG. 16.

With reference also to the example UV light-emitting module shown FIG. 13, each of the UV light-emitting modules 300 includes a sidewall ventilation opening 349 into which pressurized air within the housing 500 enters. The air passes over and through the UV light emitters 320 and other components inside the enclosures of the modules 300 and exits through a rear wall ventilation opening 352 in rear wall 308. In this example and as shown in FIGS. 17 and 19, fittings 420 affixed to the rear wall ventilation openings are extend through and are pneumatically coupled to respective housing ventilation exit openings 530, 534 in cover panel 538 and direct the exiting airflow from the modules through these openings and into atmosphere.

The two housing ventilation exit openings 530, 534 are located above the module cutouts 520, 524, respectively, in bottom panel 514 and are positioned to receive and allow the fittings 420 to extend through the openings. In this manner, the housing ventilation exit openings 530, 534 allow pressurized air within the housing 500 and UV light-emitting modules 300 to escape.

In different examples, the housing 500 can be mounted in a ceiling, wall, or other support structure, and can be utilized with stationary structures or in moveable applications, such as in a passenger or commercial vehicles, aircraft, spacecraft and the like. In some examples the housing 500 can be mounted to autonomous mobile devices such as robots.

With reference to the descriptions above, in some examples each of the UV light-emitting modules 300 within the housing 500 receives power from a common power source, such as the external power source 202 of the system 100 shown in FIG. 2.

Figure 20:
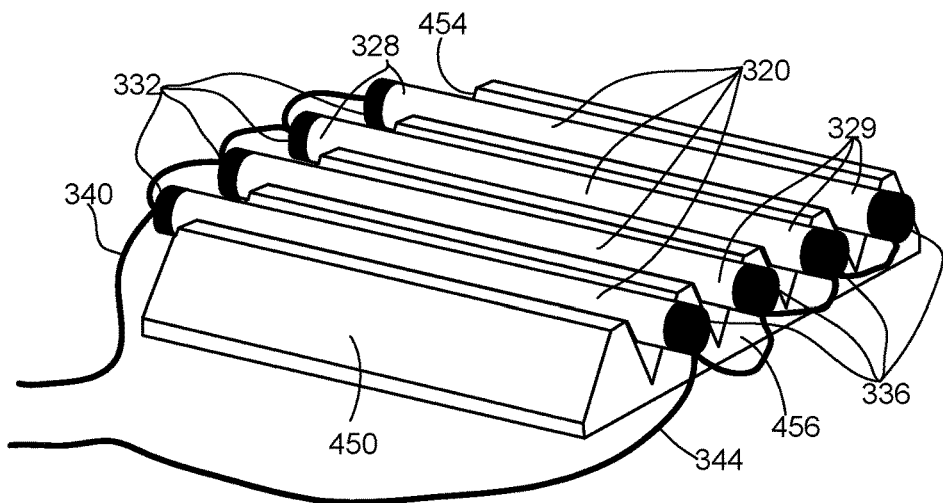
FIG. 20 shows another example of an ultraviolet (UV) light emitter support according to examples of the present disclosure.

With reference now to FIGS. 20-23, additional examples of UV light emitter supports are illustrated. As described further below, one or more of these UV light emitter supports may be utilized with any examples of the UV light-emitting modules described herein. With reference now to FIG. 20, in some examples a UV light emitter support 450 is fabricated from a fluoropolymer as a single, unitary block of material. In one example, the fluoropolymer is polytetrafluoroethylene (PTFE).

The UV light emitter support 450 has a first side 454 and an opposing second side 456. In this example, each of the UV light emitters 320 seated in the UV light emitter support 450 is an elongated lamp having a first end 328 and an opposing second end 329. The first end 328 of each of the lamps extends beyond the first side 454 of the UV light emitter support 450, and the second end of each of the lamps extends beyond the second side 456 of the UV light emitter support.

A first terminal 332 is affixed to the first end 328 of each of the elongated lamps, and a second terminal 336 is affixed to the second end 329 of each of the lamps. A first lead wire 340 electrically couples each of the first terminals 332 to a power source, and a second lead wire 344 electrically couples each of the second terminals 336 to the power source. Advantageously, in this configuration utilizing a UV light emitter support that is fabricated from a fluoropolymer, the electrodes (terminals 332, 336) are moved further apart as compared to utilizing two aluminum UV light emitter supports as described in examples above. Accordingly, this configuration enables higher voltages and correspondingly higher UV outputs prior to arcing between the terminals.

Additionally, fluoropolymer materials have dielectric properties and reflect 222 nm UV light. Accordingly, this configuration also provides a larger surface area of 222 nm UV light reflective material from which UV light emitted by the UV light emitters 320 is reflected. Further, in some examples fluoropolymer UV light emitter supports can be affixed directly to a conductive rear wall 308 of a UV light-emitting module 300, thereby avoiding the need for an electrically insulating separator between such supports and the rear wall. Additionally, because the fluoropolymer UV light emitter supports in these examples are dielectrics, the internal support surfaces of the supports can have angled or sharp edges, as opposed to radiused edges, without increasing the probability of arcing. Accordingly, these configurations may can simplify manufacturing and/or reduce associated production costs.

In other examples, two or more UV light emitter supports 450 fabricated from a fluoropolymer may be combined to seat the UV light emitters 320. In one example and with reference now to FIG. 21, three fluoropolymer UV light emitter supports 452, 455 and 457 are placed side-by-side to form a square-shaped UV light emitter support. In different examples the UV light emitter supports can have different lengths and widths, and can be combined to form a variety of shapes and sizes.

In some examples, different combinations of UV light emitter supports fabricated from conductive materials and from fluoropolymers may be utilized. With continued reference to FIG. 21, in one alternative example the UV light emitter support 455 is fabricated from a conductive material, such as aluminum, while the UV light emitter supports 452 and 457 on either side are fabricated from a fluoropolymer. In some examples and with reference to FIG. 22, where the rear wall 308 of a UV light-emitting module 300 is fabricated from a conductive material such as aluminum, a thermally conductive and electrically insulating separator 350 is provided between the UV light emitter supports 452, 455 and 457 and the rear wall.

Figure 21:
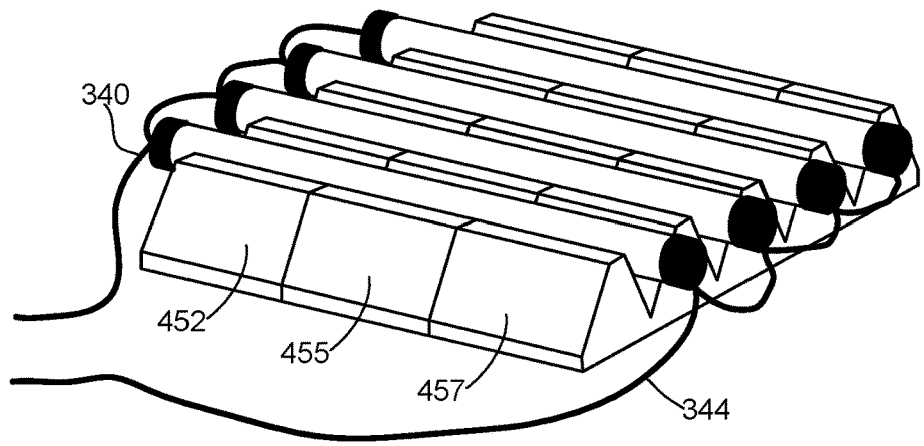
FIG. 21 shows an example of three ultraviolet (UV) light emitter supports according to examples of the present disclosure.
Figure 22:
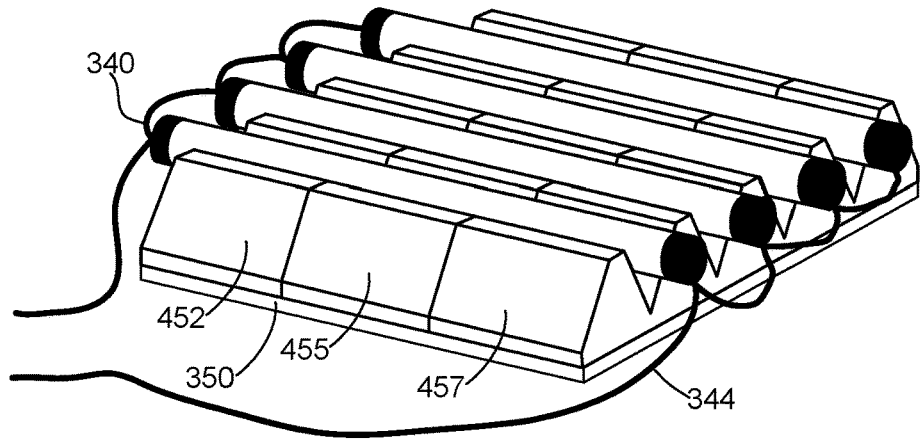
FIG. 22 shows another example of three ultraviolet (UV) light emitter supports including an electrically insulating separator according to examples of the present disclosure.

In the example of FIG. 21 and like the example described in FIG. 20, lead wires 340 and 344 electrically couple terminals of the elongated lamps to a power source. In other examples where two UV light emitter supports are fabricated from conductive materials and used with one or more fluoropolymer UV light emitter supports, and with reference to the examples shown in FIGS. 4 and 5, an electrical conductor extends through the rear wall of the UV light emitting module into each of the aluminum UV light emitter supports to provide power to the light emitters as described above.

Figure 23:
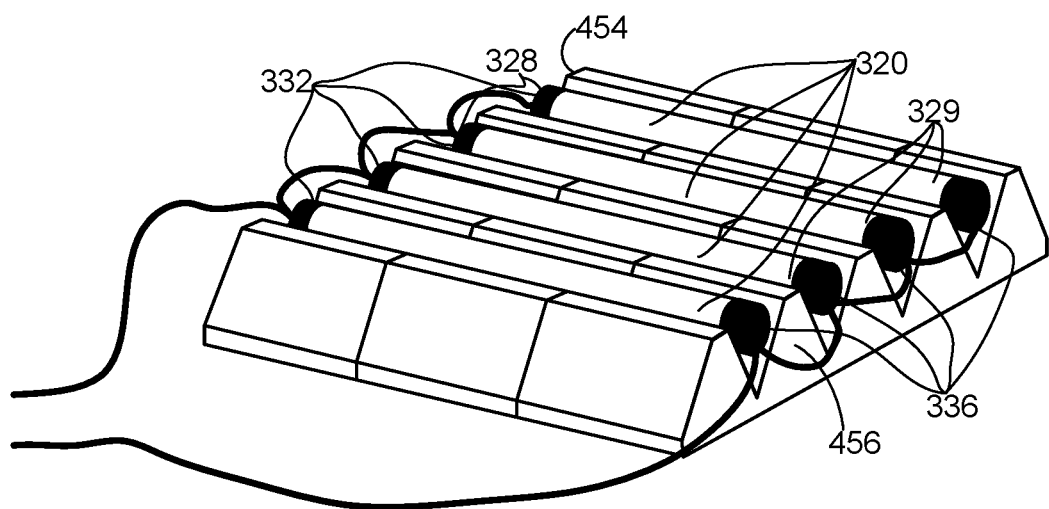
FIG. 23 shows another example of three ultraviolet (UV) light emitter supports in which the UV light emitter supports are flush with UV light emitters according to examples of the present disclosure.

With reference now to FIG. 23, in some examples the first ends 328 and second ends 329 of each of the UV light emitters 320 are substantially flush with the first side 454 and the second side 456, respectively, of the UV light emitter support. In the example of FIG. 23, the terminals 332 and 336 at the ends of the UV light emitters 320 are substantially flush with the first side 454 and the second side 456, respectively.

In different examples of UV light-emitting modules and related systems for disinfecting one or more components of the present disclosure, the modules can utilize any suitable combinations of features described herein, including but not limited to ventilation openings, heat sink features, and component materials.

Figure 24:
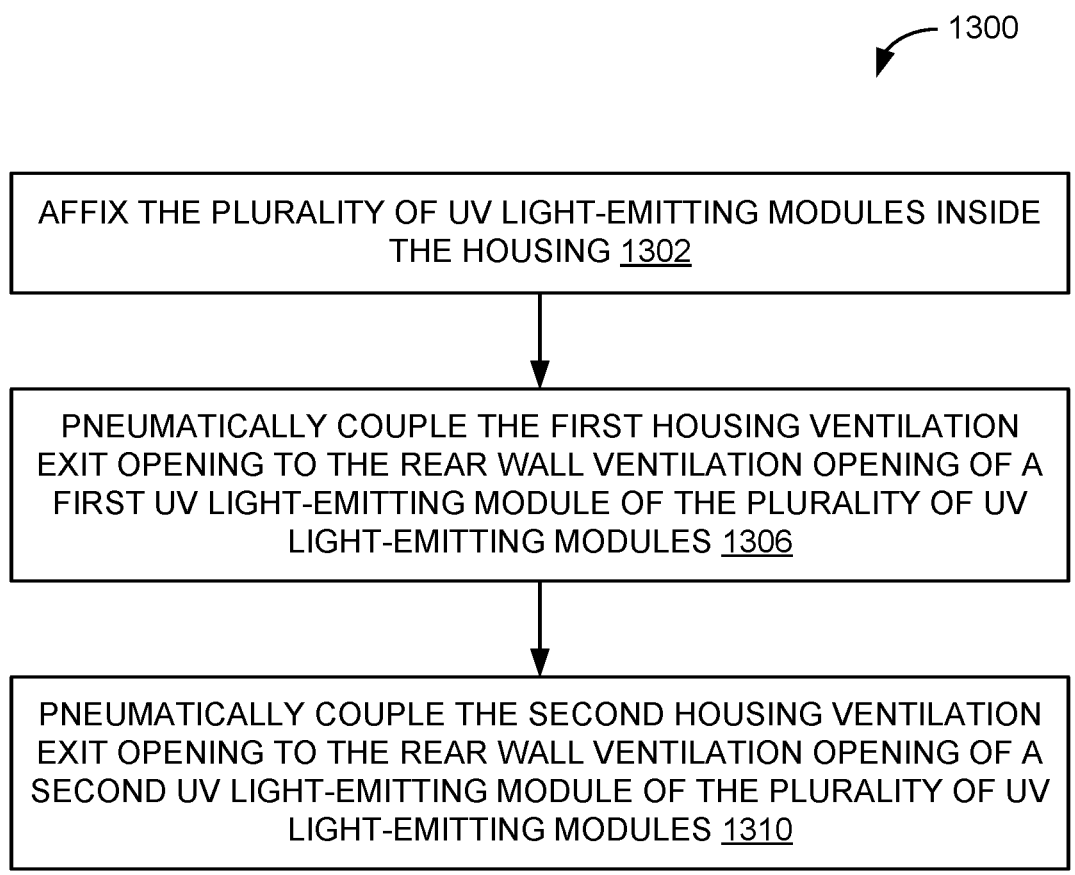
FIG. 24 shows a block diagram of an example method for assembling a system for disinfecting one or more components according to examples of the present disclosure.

Turning now to FIG. 24, a method 1300 of assembling a system for disinfecting one or more components is illustrated. The method 1300 is performed using plurality of ultraviolet (UV) light-emitting modules and a housing, wherein each of the UV light-emitting modules includes an enclosure having an aluminum rear wall with a rear wall ventilation opening. A face plate is spaced from the rear wall and includes a light-transmitting aperture. Four aluminum sidewalls extend between the rear wall and the face plate, wherein at least one sidewall of the four aluminum sidewalls comprises a sidewall ventilation opening. Each module further includes at least one fluoropolymer UV light emitter support within the enclosure and a plurality of UV light emitters within the enclosure, wherein each of the UV light emitters comprises an elongated lamp that is seated in the at least one fluoropolymer UV light emitter support. Each of the elongated lamps comprises a first end having a first terminal and an opposing second end having a second terminal. A first lead wire electrically couples the first terminal of each of the elongated lamps to a power source, and a second lead wire electrically couples the second terminal of each of the elongated lamps to the power source. The housing includes at least one cooling fan configured to direct air into the housing and at least a first housing ventilation exit opening and a second housing ventilation exit opening.

At 1302, method 1300 includes the step of affixing the plurality of UV light-emitting modules inside the housing. At 1306, the method 1300 includes the step of pneumatically coupling the first housing ventilation exit opening to the rear wall ventilation opening of a first UV light-emitting module of the plurality of UV light-emitting modules. At 1310, the method 1300 includes pneumatically coupling the second housing ventilation exit opening to the rear wall ventilation opening of a second UV light-emitting module of the plurality of UV light-emitting modules.

Figure 25:
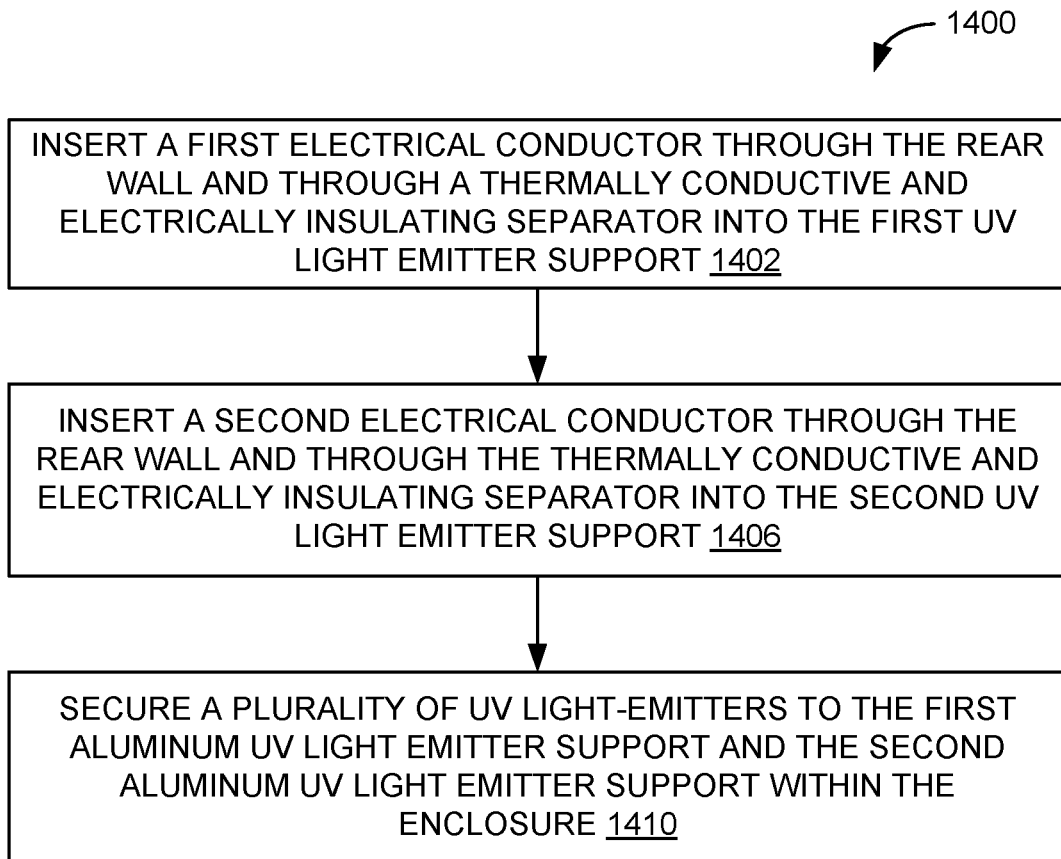
FIG. 25 shows a block diagram of an example method for assembling an ultraviolet (UV) light-emitting module for disinfecting one or more components according to examples of the present disclosure.

Turning now to FIG. 25, a method 1400 of assembling an ultraviolet (UV) light-emitting module for disinfecting one or more components is illustrated. The method 1400 is performed using an enclosure including a rear wall and a face plate spaced from the rear wall that includes a light-transmitting aperture. The enclosure also includes four sidewall that extend between the rear wall and the face plate. The method 1400 is also performed using a first UV light emitter support and a second UV light emitter support, and at least one cooling feature selected from (1) a sidewall ventilation opening in the at least one sidewall and (2) a heat sink feature extending from the rear wall.

At 1402, the method 1400 includes the step of inserting a first electrical conductor through the rear wall and through a thermally conductive and electrically insulating separator into the first UV light emitter support. At 1406, the method 1400 includes the step of inserting a second electrical conductor through the rear wall and through the thermally conductive and electrically insulating separator into the second UV light emitter support. At 1410, the method 1400 includes the step of securing a plurality of UV light emitters to the first aluminum UV light emitter support and the second aluminum UV light emitter support within the enclosure.

Figure 26:
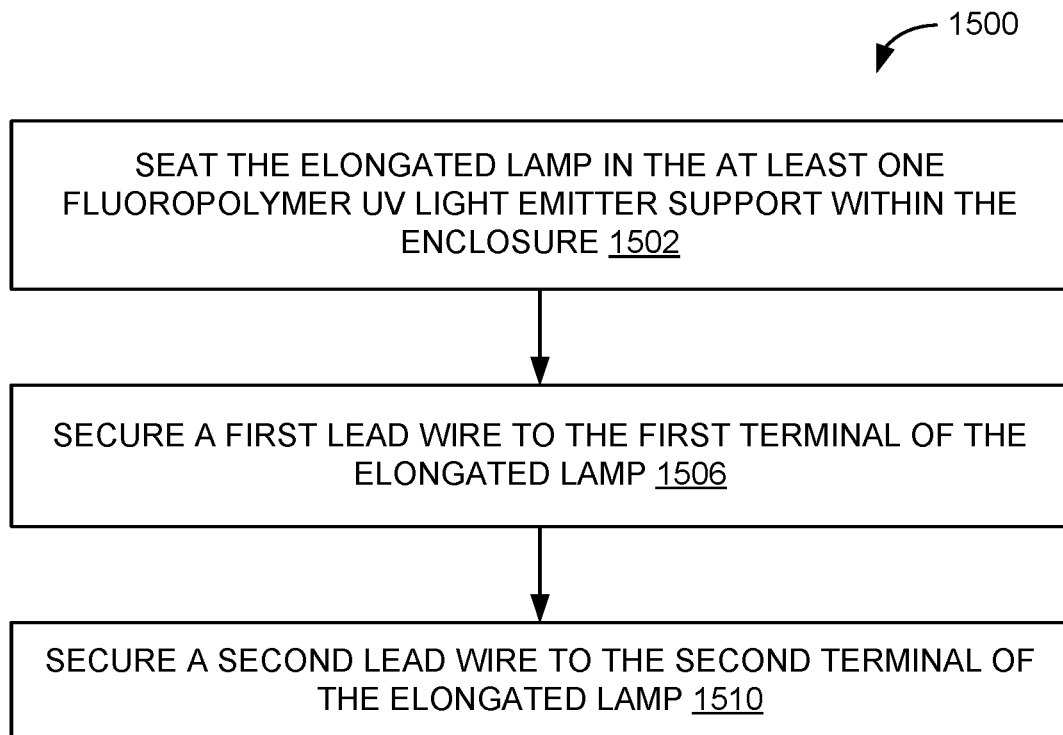
FIG. 26 shows a block diagram of another example method for assembling an ultraviolet (UV) light-emitting module for disinfecting one or more components according to examples of the present disclosure.

Turning now to FIG. 26, a method 1500 of assembling an ultraviolet (UV) light-emitting module for disinfecting one or more components is illustrated. The method 1500 is performed using an enclosure that includes a rear wall and a face plate spaced from the rear wall and having a light-transmitting aperture, and four sidewalls extending between the rear wall and the face plate, at least one UV light emitter support fabricated from a fluoropolymer, at least one cooling feature selected from (1) a sidewall ventilation opening in the at least one sidewall and (2) a heat sink feature extending from the rear wall, and at least one UV light emitter comprising an elongated lamp that comprises a first end having a first terminal and an opposing second end having a second terminal.

At 1502, the method 1500 includes the step of seating the elongated lamp in the at least one fluoropolymer UV light emitter support within the enclosure. At 1506, the method 1500 includes the step of securing a first lead wire to the first terminal of the elongated lamp. At 1510, the method 1400 includes the step of securing a second lead wire to the second terminal of the elongated lamp.

Further, the disclosure comprises configurations according to the following clauses.

Clause 1. An ultraviolet (UV) light-emitting module for disinfecting one or more components, the module comprising an enclosure comprising a rectangular aluminum rear wall comprising a rear wall ventilation opening; a rectangular face plate spaced from the rear wall and comprising a light-transmitting aperture; and four aluminum sidewalls extending between the rear wall and the face plate, wherein at least one sidewall of the four aluminum sidewalls comprises a sidewall ventilation opening; at least one fluoropolymer UV light emitter support within the enclosure; a plurality of UV light emitters within the enclosure, wherein each of the UV light emitters comprises an elongated lamp that is seated in the at least one fluoropolymer UV light emitter support, the elongated lamp comprising a first end having a first terminal and an opposing second end having a second terminal; a first lead wire electrically coupling the first terminal of each of the elongated lamps to a power source; and a second lead wire electrically coupling the second terminal of each of the elongated lamps to the power source.

Clause 2. The UV light-emitting module of clause 1, wherein the fluoropolymer is polytetrafluoroethylene (PTFE).

Clause 3. The UV light-emitting module of any of clauses 1-2, wherein the at least one fluoropolymer UV light emitter support is a single UV light emitter support.

Clause 4. The UV light-emitting module of any of clauses 1-3, wherein the at least one fluoropolymer UV light emitter support comprises two or more fluoropolymer UV light emitter supports.

Clause 5. The UV light-emitting module of clause 4, further comprising an aluminum UV light emitter support located between a first fluoropolymer UV light emitter support and a second fluoropolymer UV light emitter support.

Clause 6. The UV light-emitting module of clause 5, further comprising an electrical conductor extending through the rear wall into the aluminum UV light emitter support.

Clause 7. The UV light-emitting module of clause 6, further comprising a thermally conductive and electrically insulating separator between the aluminum UV light emitter support and the rear wall, wherein the aluminum UV light emitter support is affixed to the thermally conductive and electrically insulating separator.

Clause 8. The UV light-emitting module of clause 7, wherein the thermally conductive and electrically insulating separator has a thermal conductivity of approximately 15 international British thermal unit per hour per square foot per degree Fahrenheit (BTU)/($°$ F. Hr. Ft.$^2$) or higher.

Clause 9. The UV light-emitting module of any of clauses 1-8, wherein the at least one fluoropolymer UV light emitter support comprises a first side and an opposing second side, and for each of the elongated lamps, the first end extends beyond the first side and the second end extends beyond the second side.

Clause 10. The UV light-emitting module of any of clauses 1-9, wherein the at least one fluoropolymer UV light emitter support comprises a first side and an opposing second side, and for each of the elongated lamps, the first end is substantially flush with the first side and the second end is substantially flush with the second side.

Clause 11. The UV light-emitting module of any of clauses 1-10, further comprising a cooling fan configured to deliver air through either the sidewall ventilation opening or the rear wall ventilation opening.

Clause 12. The UV light-emitting module of any of clauses 1-11, further comprising a plurality of fins extending from the rear wall.

Clause 13. The UV light-emitting module of any of clauses 1-12, wherein each of the plurality of UV light emitters is configured to emit 222 nm wavelength UV light.

Clause 14. The UV light-emitting module of any of clauses 1-13, further comprising a low pass filter adjacent to the light-transmitting aperture of the face plate.

Clause 15. The UV light-emitting module of any of clauses 1-14, wherein each of the plurality of UV light emitters comprises an excimer lamp, the module further comprising a circuit board comprising a UV LED configured to pre-ionize gas in the excimer lamp.

Clause 16. A system for disinfecting one or more components, the system comprising: a plurality of ultraviolet (UV) light-emitting modules, wherein each of the UV light-emitting modules comprises: an enclosure comprising: a rectangular aluminum rear wall comprising a rear wall ventilation opening; a rectangular face plate spaced from the rear wall and comprising a light-transmitting aperture; and four aluminum sidewalls extending between the rear wall and the face plate, wherein at least one sidewall of the four aluminum sidewalls comprises a sidewall ventilation opening; at least one fluoropolymer UV light emitter support within the enclosure; a plurality of UV light emitters within the enclosure, wherein each of the UV light emitters comprises an elongated lamp that is seated in the at least one fluoropolymer UV light emitter support, the elongated lamp comprising a first end having a first terminal and an opposing second end having a second terminal; a first lead wire electrically coupling the first terminal of each of the elongated lamps to a power source; and a second lead wire electrically coupling the second terminal of each of the elongated lamps to the power source; and a housing that encloses the plurality of UV light-emitting modules, the housing comprising at least one cooling fan that directs air into the housing and at least one housing ventilation exit opening through which air escapes.

Clause 17. The system of clause 16, wherein the fluoropolymer is polytetrafluoroethylene (PTFE).

Clause 18. The system of any of clauses 16-17, wherein the at least one fluoropolymer UV light emitter support is a single UV light emitter support.

Clause 19. The system of any of clauses 16-18, wherein the at least one fluoropolymer UV light emitter support comprises two or more fluoropolymer UV light emitter supports.

Clause 20. A method of assembling a system for disinfecting one or more components, the method performed using plurality of ultraviolet (UV) light-emitting modules and a housing, wherein each of the UV light-emitting modules includes an enclosure having an aluminum rear wall with a rear wall ventilation opening, a face plate spaced from the rear wall and having a light-transmitting aperture, four aluminum sidewalls extending between the rear wall and the face plate, wherein at least one sidewall of the four aluminum sidewalls comprises a sidewall ventilation opening, and each module further includes at least one fluoropolymer UV light emitter support within the enclosure, a plurality of UV light emitters within the enclosure, wherein each of the UV light emitters comprises an elongated lamp that is seated in the at least one fluoropolymer UV light emitter support, the elongated lamp comprising a first end having a first terminal and an opposing second end having a second terminal, a first lead wire electrically coupling the first terminal of each of the elongated lamps to a power source, and a second lead wire electrically coupling the second terminal of each of the elongated lamps to the power source, and wherein the housing includes at least one cooling fan configured to direct air into the housing and at least a first housing ventilation exit opening and a second housing ventilation exit opening, the method comprising: affixing the plurality of UV light-emitting modules inside the housing; pneumatically coupling the first housing ventilation exit opening to the rear wall ventilation opening of a first UV light-emitting module of the plurality of UV light-emitting modules; and pneumatically coupling the second housing ventilation exit opening to the rear wall ventilation opening of a second UV light-emitting module of the plurality of UV light-emitting modules.

The subject disclosure includes all novel and non-obvious combinations and subcombinations of the various features and techniques disclosed herein. The various features and techniques disclosed herein are not necessarily required of all examples of the subject disclosure. Furthermore, the various features and techniques disclosed herein may define patentable subject matter apart from the disclosed examples and may find utility in other implementations not expressly disclosed herein.

The invention claimed is:

1. An ultraviolet (UV) light-emitting module for disinfecting one or more components, the UV light-emitting module comprising:
   an enclosure comprising:
      a rectangular aluminum rear wall comprising a rear wall ventilation opening;
      a rectangular face plate spaced from the rear wall and comprising a light-transmitting aperture; and
      four aluminum sidewalls extending between the rear wall and the face plate, wherein at least one sidewall of the four aluminum sidewalls comprises a sidewall ventilation opening;
   at least one fluoropolymer UV light emitter support within the enclosure, the at least one fluoropolymer UV light emitter support comprising a plurality of first seating surfaces and a plurality of second seating surfaces at least partially facing the first seating surfaces;
   a plurality of UV light emitters within the enclosure, wherein each of the UV light emitters comprises an elongated lamp that is seated in the at least one fluoropolymer UV light emitter support against one of the first seating surfaces and one of the second seating surfaces, the elongated lamp comprising a first end having a first terminal and an opposing second end having a second terminal;
   a first lead wire electrically coupling the first terminal of each of the elongated lamps to a power source; and
   a second lead wire electrically coupling the second terminal of each of the elongated lamps to the power source.

2. The UV light-emitting module of claim 1, wherein the at least one fluoropolymer UV light emitter support comprises a fluoropolymer, wherein the fluoropolymer is polytetrafluoroethylene (PTFE).

3. The UV light-emitting module of claim 1, wherein the at least one fluoropolymer UV light emitter support is a single UV light emitter support.

4. The UV light-emitting module of claim 1, wherein the at least one fluoropolymer UV light emitter support comprises two or more fluoropolymer UV light emitter supports.

5. The UV light-emitting module of claim 4, further comprising an aluminum UV light emitter support located between a first fluoropolymer UV light emitter support and a second fluoropolymer UV light emitter support.

6. The UV light-emitting module of claim 5, further comprising an electrical conductor extending through the rear wall into the aluminum UV light emitter support.

7. The UV light-emitting module of claim 6, further comprising a thermally conductive and electrically insulating separator between the aluminum UV light emitter support and the rear wall, wherein the aluminum UV light emitter support is affixed to the thermally conductive and electrically insulating separator.

8. The UV light-emitting module of claim 7, wherein the thermally conductive and electrically insulating separator has a thermal conductivity of approximately 15 BTU/° F. Hr. Ft.$^2$ or higher.

9. The UV light-emitting module of claim 1, wherein the at least one fluoropolymer UV light emitter support comprises a first side and an opposing second side, and for each of the elongated lamps, the first end extends beyond the first side and the second end extends beyond the second side.

10. The UV light-emitting module of claim 1, wherein the at least one fluoropolymer UV light emitter support comprises a first side and an opposing second side, and for each of the elongated lamps, the first end is substantially flush with the first side and the second end is substantially flush with the second side.

11. The UV light-emitting module of claim 1, further comprising a cooling fan configured to deliver air through either the sidewall ventilation opening or the rear wall ventilation opening.

12. The UV light-emitting module of claim 1, further comprising a plurality of fins extending from the rear wall.

13. The UV light-emitting module of claim 1, wherein each of the plurality of UV light emitters is configured to emit 222 nanometer (nm) wavelength UV light.

14. The UV light-emitting module of claim 1, further comprising a low pass filter adjacent to the light-transmitting aperture of the face plate.

15. The UV light-emitting module of claim 1, wherein each of the plurality of UV light emitters comprises an excimer lamp, the UV light-emitting module further comprising a circuit board comprising a UV light-emitting diode (LED) configured to pre-ionize gas in the excimer lamp.

16. A system for disinfecting one or more components, the system comprising:
   a plurality of ultraviolet (UV) light-emitting modules, wherein each of the UV light-emitting modules comprises:
      an enclosure comprising:
         a rectangular aluminum rear wall comprising a rear wall ventilation opening;
         a rectangular face plate spaced from the rear wall and comprising a light-transmitting aperture; and
         four aluminum sidewalls extending between the rear wall and the face plate, wherein at least one sidewall of the four aluminum sidewalls comprises a sidewall ventilation opening;
      at least one fluoropolymer UV light emitter support within the enclosure, the at least one fluoropolymer UV light emitter support comprising a plurality of first seating surfaces and a plurality of second seating surfaces at least partially facing the first seating surfaces;
      a plurality of UV light emitters within the enclosure, wherein each of the UV light emitters comprises an elongated lamp that is seated in the at least one fluoropolymer UV light emitter support against one of the first seating surfaces and one of the second seating surfaces, the elongated lamp comprising a first end having a first terminal and an opposing second end having a second terminal;
      a first lead wire electrically coupling the first terminal of each of the elongated lamps to a power source; and
      a second lead wire electrically coupling the second terminal of each of the elongated lamps to the power source; and a housing that encloses the plurality of UV light-emitting modules, the housing comprising at least one cooling fan that directs air into the housing and at least one housing ventilation exit opening through which air escapes.

17. The system of claim 16, wherein the at least one fluoropolymer UV light emitter support comprises a fluoropolymer, wherein the fluoropolymer is polytetrafluoroethylene (PTFE).

18. The system of claim 16, wherein the at least one fluoropolymer UV light emitter support is a single UV light emitter support.

19. The system of claim 16, wherein the at least one fluoropolymer UV light emitter support comprises two or more fluoropolymer UV light emitter supports.

20. A method of assembling a system for disinfecting one or more components, the method performed using a plurality of ultraviolet (UV) light-emitting modules and a housing, wherein each of the UV light-emitting modules includes an enclosure having an aluminum rear wall with a rear wall ventilation opening, a face plate spaced from the rear wall and having a light-transmitting aperture, four aluminum sidewalls extending between the rear wall and the face plate, wherein at least one sidewall of the four aluminum sidewalls comprises a sidewall ventilation opening, and each module further includes at least one fluoropolymer UV light emitter support within the enclosure, the at least one fluoropolymer UV light emitter support comprising a plurality of first seating surfaces and a plurality of second seating surfaces at least partially facing the first seating surfaces, a plurality of UV light emitters within the enclosure, wherein each of the UV light emitters comprises an elongated lamp that is seated in the at least one fluoropolymer UV light emitter support against one of the first seating surfaces and one of the second seating surfaces, the elongated lamp comprising a first end having a first terminal and an opposing second end having a second terminal, a first lead wire electrically coupling the first terminal of each of the elongated lamps to a power source, and a second lead wire electrically coupling the second terminal of each of the elongated lamps to the power source, and wherein the housing includes at least one cooling fan configured to direct air into the housing and at least a first housing ventilation exit opening and a second housing ventilation exit opening, the method comprising:

affixing the plurality of UV light-emitting modules inside the housing;

pneumatically coupling the first housing ventilation exit opening to the rear wall ventilation opening of a first UV light-emitting module of the plurality of UV light-emitting modules; and pneumatically coupling the second housing ventilation exit opening to the rear wall ventilation opening of a second UV light-emitting module of the plurality of UV light-emitting modules.

\* \* \* \* \*